US011828709B2

United States Patent
Sun et al.

(10) Patent No.: US 11,828,709 B2
(45) Date of Patent: Nov. 28, 2023

(54) ANALYTICAL SYSTEM FOR MOLECULE DETECTION AND SENSING

(71) Applicant: GeneSense Technology Limited, Grand Cayman (KY)

(72) Inventors: Yinghua Sun, Shanghai (CN); Mei Yan, Shanghai (CN)

(73) Assignee: GENESENSE TECHNOLOGY INC., Shanghai (CN)

( * ) Notice: Subject to any disclaimer, the term of this patent is extended or adjusted under 35 U.S.C. 154(b) by 0 days.

(21) Appl. No.: 16/651,322

(22) PCT Filed: May 17, 2019

(86) PCT No.: PCT/CN2019/087455
§ 371 (c)(1),
(2) Date: Mar. 26, 2020

(87) PCT Pub. No.: WO2020/232581
PCT Pub. Date: Nov. 26, 2020

(65) Prior Publication Data
US 2022/0074859 A1    Mar. 10, 2022

(51) Int. Cl.
*G01N 21/64*    (2006.01)
*G01N 21/77*    (2006.01)
(Continued)

(52) U.S. Cl.
CPC ..... *G01N 21/6456* (2013.01); *G01N 21/6428* (2013.01); *G01N 2021/6439* (2013.01); *G01N 2201/08* (2013.01)

(58) Field of Classification Search
None
See application file for complete search history.

(56) References Cited

U.S. PATENT DOCUMENTS 6,469,785 B1    10/2002    Duveneck et al.
8,697,435 B2    4/2014    Heil et al.
(Continued)

FOREIGN PATENT DOCUMENTS

CN    101960293 A    1/2011
CN    105300955 A    2/2016
(Continued)

OTHER PUBLICATIONS

Altkorn et al., "Low-loss liquid-core optical fiber for low-refractive-index liquids: fabrication, characterization, and application in Raman spectroscopy," Applied optics, vol. 36, No. 34, 1997, pp. 8992-8998.
(Continued)

*Primary Examiner* — Neil N Turk
(74) *Attorney, Agent, or Firm* — Mauriel Kapouytian Woods LLP; Liang Huang

(57) ABSTRACT

The present disclosure describes a system for analyzing biological samples. The system includes an optical waveguide. The optical waveguide includes a first end and a second end. The optical waveguide is configured to receive an excitation light at the first end. The optical waveguide further includes a first light-guiding layer disposed between the first end and the second end. The first light-guiding layer is configured to direct, at least in part, the received excitation light toward the second end of the optical waveguide along a longitudinal direction of the optical waveguide. The optical waveguide further includes a fluidic reaction channel bounded in part by the first light-guiding layer of the optical waveguide, which delivers the excitation light to biological samples disposed in the fluidic reaction channel. The system further includes a backside illumination based image sensor.

19 Claims, 13 Drawing Sheets

(51) Int. Cl.
*G01N 33/543* (2006.01)
*H01L 27/146* (2006.01)

(56) References Cited

U.S. PATENT DOCUMENTS

| | | | |
|---|---|---|---|
| 8,906,320 | B1 | 12/2014 | Eltoukhy et al. |
| 8,936,763 | B2 | 1/2015 | Rothberg et al. |
| 9,291,568 | B2 | 3/2016 | McCaffrey et al. |
| 9,658,161 | B2 | 5/2017 | Saxena et al. |
| 9,778,191 | B2 | 10/2017 | Hsieh et al. |
| 9,921,157 | B2 | 3/2018 | Rothberg et al. |
| 9,961,291 | B2 | 5/2018 | Chen |
| 10,165,211 | B1* | 12/2018 | Borthakur ............ H04N 25/702 |
| 10,254,225 | B2 | 4/2019 | Zhong et al. |
| 10,267,733 | B2 | 4/2019 | Dorpe et al. |
| 2007/0145236 | A1* | 6/2007 | Kiesel ................... G01J 1/4228 356/226 |
| 2008/0043242 | A1* | 2/2008 | Emmerson ......... G01N 21/4133 356/450 |
| 2012/0021525 | A1* | 1/2012 | Fehr ..................... G01N 21/648 250/226 |
| 2015/0119259 | A1 | 4/2015 | Ju et al. |
| 2015/0268162 | A1* | 9/2015 | Lear ..................... H01L 31/105 356/128 |
| 2015/0311376 | A1 | 10/2015 | Yu |
| 2016/0363728 | A1 | 12/2016 | Wang et al. |
| 2018/0155782 | A1 | 6/2018 | Zhong |

FOREIGN PATENT DOCUMENTS

| | | |
|---|---|---|
| CN | 106796322 A | 5/2017 |
| WO | 2015056028 A1 | 4/2015 |
| WO | 2018085642 A1 | 5/2018 |

OTHER PUBLICATIONS

Schmitt et al., "Evanescent field sensors based on tantalum pentoxide waveguides—a review," Sensors, vol. 8, No. 2, 2008, pp. 711-738.
Schmitt et al., "High-refractive-index waveguide platforms for chemical and biosensing," Optical Guided-wave Chemical and Biosensors I, 2010, pp. 21-54.
Fossum et al., "The Quanta Image Sensor: Every Photon Counts," Sensors, vol. 16, No. 8, 2016, 25 pages.
International Search Report and Written Opinion issued in International Application No. PCT/CN2019/087455 dated Feb. 19, 2020, 11 pages.
Tinguely et al., "Silicon nitride waveguide platform for fluorescence microscopy of living cells," Optics express, vol. 25, No. 22, 2017, pp. 27678-27690.
Frey et al., "Color filters including infrared cut-off integrated on CMOS image sensor," Optics express, vol. 19, No. 14, 2011, pp. 13073-13080.
Yang et al., "Optical properties of Teflon® AF amorphous fluoropolymers," Journal of Micro/Nanolithography, MEMS, and MOEMS, vol. 7, No. 3, 2008, 9 pages.
Oxford Nanopore Technologies, https://nanoporetech.com/products/minion, 2020, 1 page.
Oxford Nanopore Technologies, https://nanoporetech.com/products/gridion, 2020, 1 page.

* cited by examiner

ANALYTICAL SYSTEM FOR MOLECULE DETECTION AND SENSING

CROSS REFERENCE TO RELATED APPLICATIONS

This application is a U.S. National Phase application under 35 U.S.C. § 371 of International Application Number PCT/CN2019/087455 filed on May 17, 2019. The entire contents of these applications are hereby incorporated herein by reference for all purposes.

FIELD OF THE DISCLOSURE

The present disclosure generally relates to biomedical sample analytical systems and, more specifically, to systems for providing scalable, high speed, and high throughput molecule detection and analysis.

BACKGROUND

Biological sample analytical systems are used for various applications such as nucleic acid sequencing applications. Some of these applications may require high throughput and scalability. In typical existing analytical systems, for high throughput sequencing applications, conventional optical microscopic systems can be used to perform large area scanning. Such conventional systems are usually bulky, complicated, and associated with high instrument cost with very demanding maintenance. For low throughput applications, smaller instruments using CMOS (complementary metal-oxide-semiconductor) sensors for direct imaging are often used. But these smaller instruments have very limited data readout. Further, these types of conventional systems are not easily scalable to perform parallel detection of a large area without a scanning process (e.g., a time-consuming sequential scanning process). These existing systems are thus often either associated with low efficiency or high instrument cost. Therefore, a faster, smaller in size, easily scalable, and more photonic detection-efficient, and more cost-efficient analytical system is desired.

SUMMARY OF THE DISCLOSURE

The following presents a simplified summary of one or more examples in order to provide a basic understanding of the disclosure. This summary is not an extensive overview of all contemplated examples, and is not intended to either identify key or critical elements of all examples or delineate the scope of any or all examples. Its purpose is to present some concepts of one or more examples in a simplified form as a prelude to the more detailed description that is presented below.

In accordance with some embodiments, a system for analyzing biological samples is provided. The system includes an optical waveguide. The optical waveguide includes a first end and a second end. The optical waveguide is configured to receive an excitation light at the first end of the optical waveguide. The optical waveguide further includes a first light-guiding layer disposed between the first end and the second end. The first light-guiding layer is configured to direct, at least in part, the received excitation light toward the second end of the optical waveguide along a longitudinal direction of the optical waveguide. The optical waveguide further includes a fluidic reaction channel bounded in part by the first light-guiding layer of the optical waveguide. The fluidic reaction channel is configured to exchange liquid reagent. The optical waveguide is configured to deliver the excitation light to biological samples disposed in the fluidic reaction channel. The system for analyzing biological samples further includes an image sensor optically coupled to the optical waveguide. The image sensor is configured to detect at least a portion of light emitted from the biological samples as a result of the excitation light. The image sensor includes a plurality of photosensitive elements disposed at a first distance to the optical waveguide, and a plurality of conducting layers disposed at a second distance to the optical waveguide. The first distance is less than the second distance.

In accordance with some embodiments, a system for analyzing biological samples is provided. The system includes a plurality of liquid photonic systems. Each of the liquid photonic systems includes an optical waveguide. The optical waveguide includes a first end and a second end. The optical waveguide is configured to receive an excitation light at the first end of the optical waveguide. The optical waveguide further includes a first light-guiding layer disposed between the first end and the second end. The first light-guiding layer is configured to direct, at least in part, the received excitation light toward the second end of the optical waveguide along a longitudinal direction of the optical waveguide. The optical waveguide further includes a fluidic reaction channel bounded in part by the first light-guiding layer of the optical waveguide. The fluidic reaction channel is configured to exchange liquid reagents. The optical waveguide is configured to deliver the excitation light to biological samples disposed in the fluidic reaction channel. The liquid photonic system further includes an image sensor optically coupled to the optical waveguide. The image sensor is configured to detect at least a portion of light emitted from the biological samples as a result of the excitation light. The image sensor includes a plurality of photosensitive elements disposed at a first distance to the optical waveguide, and a plurality of conducting layers disposed at a second distance to the optical waveguide. The first distance is less than the second distance. In some embodiments, the system for analyzing biological samples further a plurality of adaptors. Each adaptor includes an adaptor optical waveguide optically coupled to an optical waveguide of a preceding liquid photonic system and an optical waveguide of a following liquid photonic system. The adaptor optical waveguide is configured to deliver the excitation light from the preceding liquid photonic system to the following liquid photonic system. The adaptor optical waveguide includes an adaptor fluidic channel. The adaptor fluidic channel is coupled to a fluidic reaction channel of a preceding liquid photonic system and a fluidic reaction channel of a following liquid photonic system. The adaptor fluidic channel is configured to deliver reagents from the preceding liquid photonic system to the following liquid photonic system.

BRIEF DESCRIPTION OF THE DRAWINGS

For a better understanding of the various described aspects, reference should be made to the description below, in conjunction with the following figures in which like-referenced numerals refer to corresponding parts throughout the figures.

DETAILED DESCRIPTION

Figure 1:
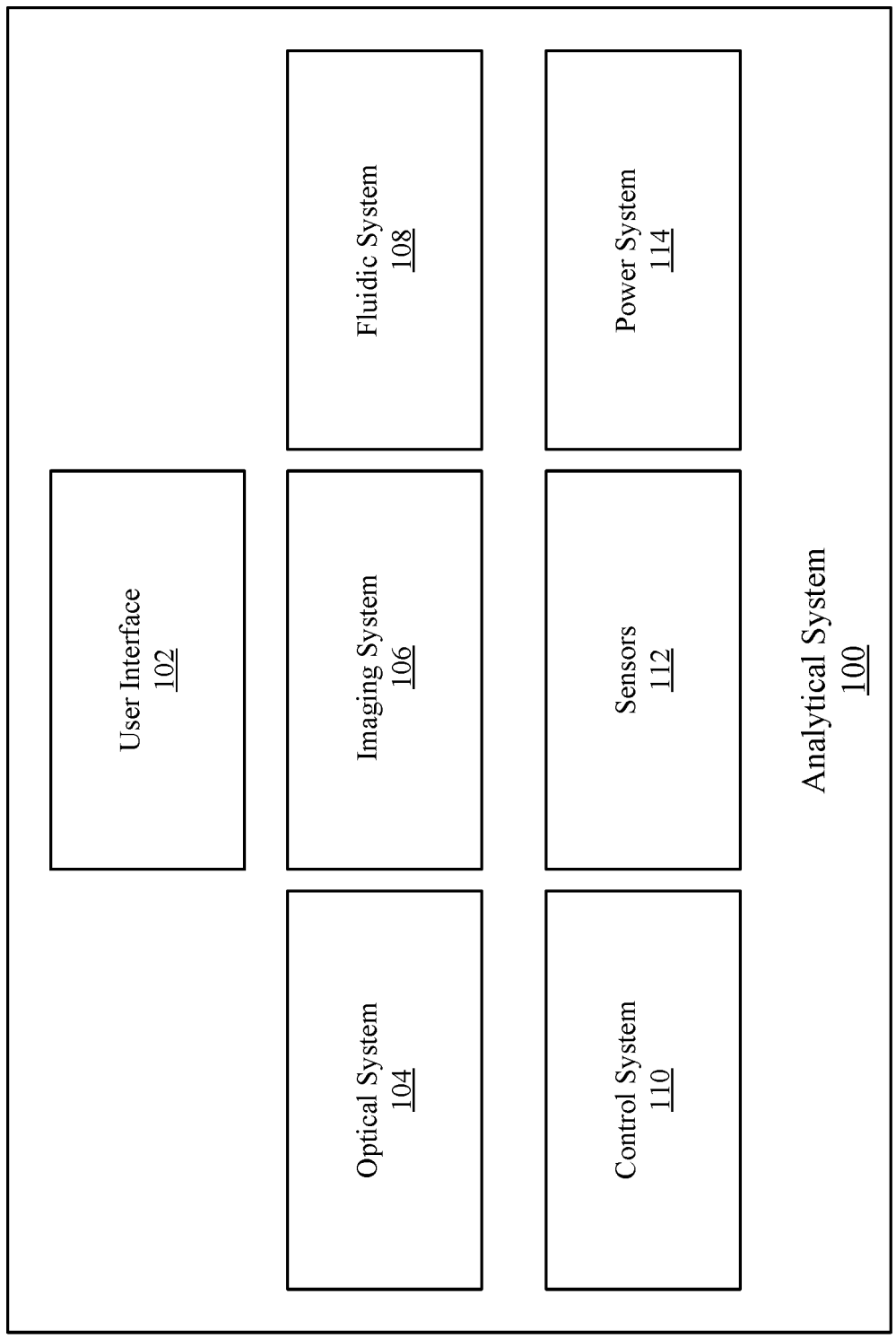
FIG. 1 is a block diagram illustrating an exemplary analytical system.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

Exemplary sample analytical systems will now be presented with reference to various elements of apparatus and methods. These apparatus and methods will be described in the following detailed description and illustrated in the accompanying drawing by various blocks, components, circuits, steps, processes, algorithms, etc. (collectively referred to as "elements"). These elements may be implemented using mechanical components, optical components, electronic hardware, computer software, or any combination thereof. Whether such elements are implemented as hardware or software depends upon the particular application and design constraints imposed on the overall system.

A conventional microscopy analytical system has limited optical field of view (e.g., 1×1 mm$^2$) at high sensitivity for collecting photons emitted from samples as a result of excitation or illumination. This kind of system relies on a scanning process to increase overall detection area (e.g., 20×150 mm$^2$), which often requires complicated mechanical systems associated with high cost and complexity. Increasing the optical field of view and eliminating scanning process is thus desired. Recent low cost analytical systems using CMOS sensor-based directly imaging techniques have opened the possibility for slightly enlarged field of view (e.g., 5×5 mm$^2$). This type of instrument eliminates scanning process with the advantages of low cost and easy operation. But this type of instrument usually has a low data readout.

Providing large detection area at low cost, high data readout, and easy usage can be very beneficial for molecular detection. The techniques described in this application use large scale back-side illumination (BSI) based CMOS image sensors (also referred to as BSI CIS) and planar photonic waveguide illumination (PWI) techniques. These techniques described in details below thus provide a scalable, high speed, and high throughput system at low instrument cost. The combination of the technologies enables large-scale fluorescence detection (e.g., greater than 50M pixel and over 500M pixel array, area over 50×100 mm$^2$) and imaging, while maintaining a compact design with low cost. In some embodiments, the photonic waveguide illumination techniques and the BSI-based image sensing technologies can be included or integrated in a liquid photonic system (e.g., one or more chips). The liquid photonic system can provide photon excitation of samples, chemical reaction in a fluidic reaction chamber, optical waveguide for directing excitation light, and image sensing. The liquid photonic system can be integrated in a single chip, PCB, or module (also referred to as a flow cell). The liquid photonic system can be used in, for example, DNA/protein array detection and other biosensor analysis. The liquid photonic system, along with other systems, are described in detail below.

Furthermore, in contrast to conventional FSI-based image sensing techniques, the photonic waveguide illumination techniques and the BSI-based image sensing techniques described in this application can greatly reduce photon cross talk and improve signal-to-noise ratio. For example, the photonic waveguide illumination can provide low background noise and high excitation power density in fluorescence detection, thereby boosting the signal-to-noise ratio. As a result, the techniques described in this application enable high performance sample analysis and highly-efficient image sensing.

FIG. 1 is a block diagram illustrating an exemplary analytical system 100. As illustrated in FIG. 1, analytical system 100 can include a user interface 102, an optical system 104, an imaging system 106, a fluidic system 108, a control system 110, sensors 112, and a power system 114. In some embodiments, user interface 102 enables interaction between analytical system 100 and a human user, in order to allow operation and control of analytical system 100 by the user and to provide information and status of the operation to the user. User interface 102 can receive physical inputs (e.g., touch- or key-based inputs) and/or speech inputs from the user; and can provide visual display and/or audible outputs of information to the user.

As shown in FIG. 1, optical system 104, imaging system 106, and sensors 112 can be configured to perform various functions including providing an excitation light, guiding or directing the excitation light in an optical waveguide, detecting light emitted from samples as a result of the excitation light, and converting photons of the detected light to electrical signals. Various embodiments of optical system 104, imaging system 106, and sensors 112 are described in more detail below using, for example, FIGS. 3A-3D. It is appreciated that optical system 104, imaging system 106, and sensors 112 may be separate systems or components; or may be integrated with one another. The combination of at least a portion of optical system 104, imaging system 106, and sensors 112 is sometimes also referred to as a flow cell or a liquid photonic system, which is described in more detail below.

Figure 2:
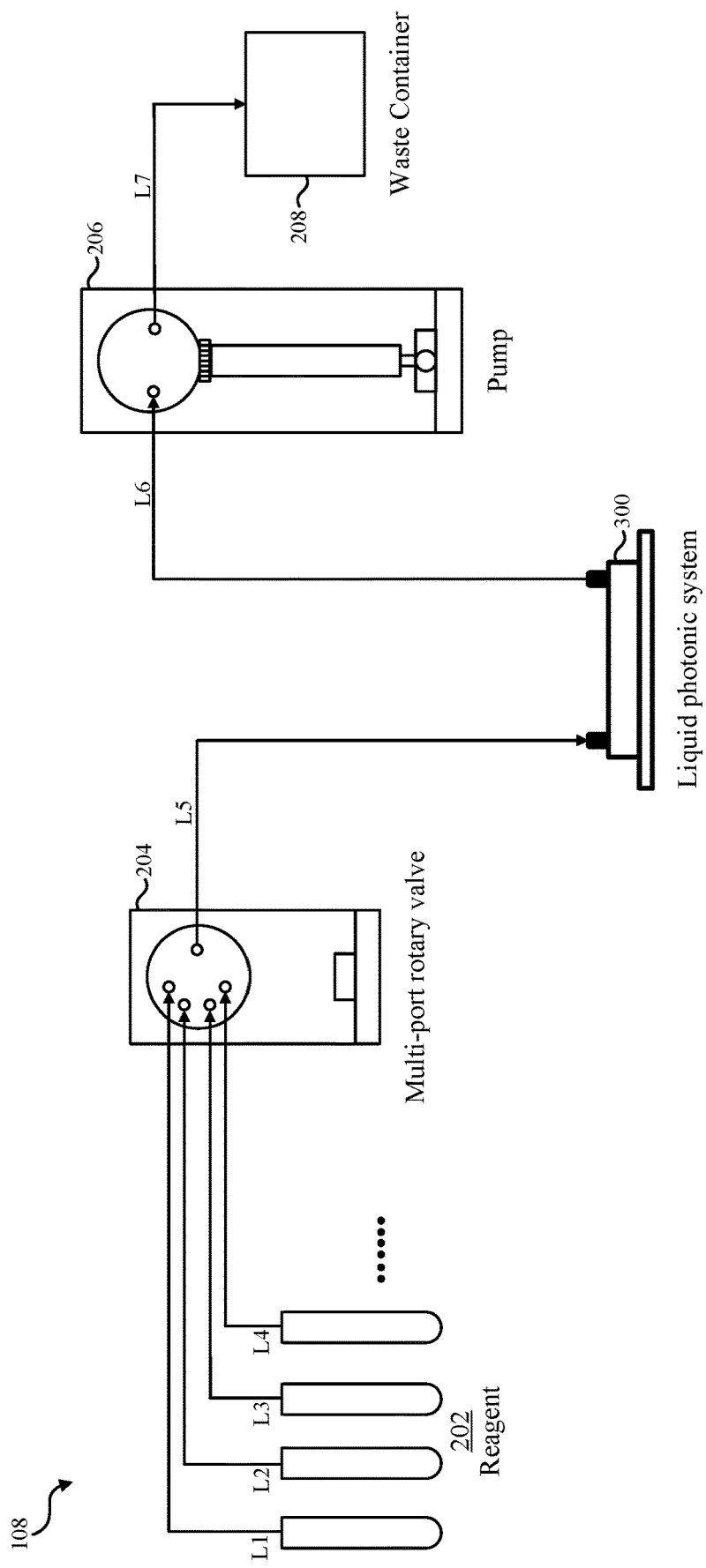
FIG. 2 illustrates an exemplary fluidic system including various sub-systems or components for delivering and exchanging sequencing reagent and for analyzing biological samples included in the sequencing reagent.

With reference to FIG. 1, fluidic system 108 can deliver reagents to a liquid photonic system, perform reagent exchange or mixing, and dispose of waste generated from the liquid photonic system. FIG. 2 illustrates an exemplary fluidic system 108 (also referred to as a microfluidics system). As illustrated in FIG. 2, fluidic system 108 can include one or more reagents 202, a multi-port rotary valve 204, a pump 206, and a waste container 208. Fluidic system 108 can deliver reagents to a liquid photonic system 300 (e.g., include a combination of at least a portion of optical system 104, imaging system 106, and sensors 112).

With reference to FIG. 2, in some embodiments, one or more reagents 202 can be sequencing reagents in which sequencing samples are disposed (e.g., in a fluidic reaction channel of liquid photonic system 300). Different reagents (e.g., L1-L4 shown in FIG. 2) can include the same or different chemicals or solutions for testing different samples, as described below. It is appreciated that different biological samples that can be tested using the systems described in this application (e.g., the fluidic system 108 and liquid photonic system 300) include, for example, luminescent or luminescently-labeled biomolecules such as nucleic acids, nucleotides, deoxyribonucleic acid (DNA), ribonucleic acid (RNA), peptide, or proteins. In some embodiments, luminescent or luminescently-labeled biomolecules can include luminescent markers capable of emitting light in one, two, or three wavelength ranges (e.g., emitting red and yellow lights) when the biomolecules are provided with an excitation light. The emitted light can be further processed (e.g., filtered) before they reach the image sensors.

With reference to FIG. 2, fluidic system 108 can deliver (e.g., using pump 206) one or more reagents (e.g., sequencing reagents) 202 to multi-port rotary valve 204. Pump 206 can be, for example, a syringe pump. In some embodiments, reagents 202 include different types of reagents (e.g., different buffer solutions or different chemicals). Multi-port rotary valve 204 can be configured or controlled (e.g., using control system 110 shown in FIG. 1) such that different reagents 202 are delivered to liquid photonic system 300 for testing in sequence. For example, reagent L1 may be delivered first, followed by reagents L2, L3, and L4. In some embodiments, multi-port rotary valve 204 and pump 206 can be configured or controlled (e.g., using control system 110 shown in FIG. 1) such that multiple reagents are separated by air gaps. Separation of the reagents by air gaps prevents or reduces the likelihood that reagents and/or samples contained therein are unintentionally mixed. This not only prevents testing samples with improper reagents, but also enables the reagents to be reused (e.g., different reagents L1-L4 as shown in FIG. 1 are not mixed and can thus be reused).

As shown in FIG. 2 and described above, pump 206 can facilitate the delivery of reagents to liquid photonic system 300 via multi-port rotary valve 204. In some embodiments, the chemical waste generated from the sample test performed by liquid photonic system 300 can be disposed by pump 206 to waste container 208. Various embodiments of liquid photonic system 300 is described in detail below. As illustrated in FIG. 2, fluid system 108 and liquid photonic system 300, along with other systems shown in FIG. 1 (e.g., control system 110 and power system 114), can perform sequential testing of multiple samples in a high speed, high throughput and highly efficient manner. Moreover, in some embodiments, only a small portion of the reagent is disposed as waste. As described above, different reagents can be separated by air gaps generated by fluidic system 108 and therefore the technologies described here enable reusing the reagent for cost saving purposes.

With reference back to FIG. 1, analytical system 100 can further include a control system 110 and a power system 114. Control system 110 can be configured (e.g., via software) to control various aspects of the analytical system 100. For example, control system 110 can include hardware and software to control the operation of optical system 104 (e.g., control the excitation light generation) and fluidic system 108 (e.g., control the multi-port rotary valve 204 and pump 206), and power system 114 (e.g., control the power supply of the various systems shown in FIG. 1). It is appreciated that various systems of analytical system 100 in FIG. 1 are for illustration only. Analytical system 100 can include more or less systems than shown in FIG. 1. Moreover, one or more systems included in analytical system 100 can be combined, integrated, or separated in any manner that is desired.

Figure 3A:
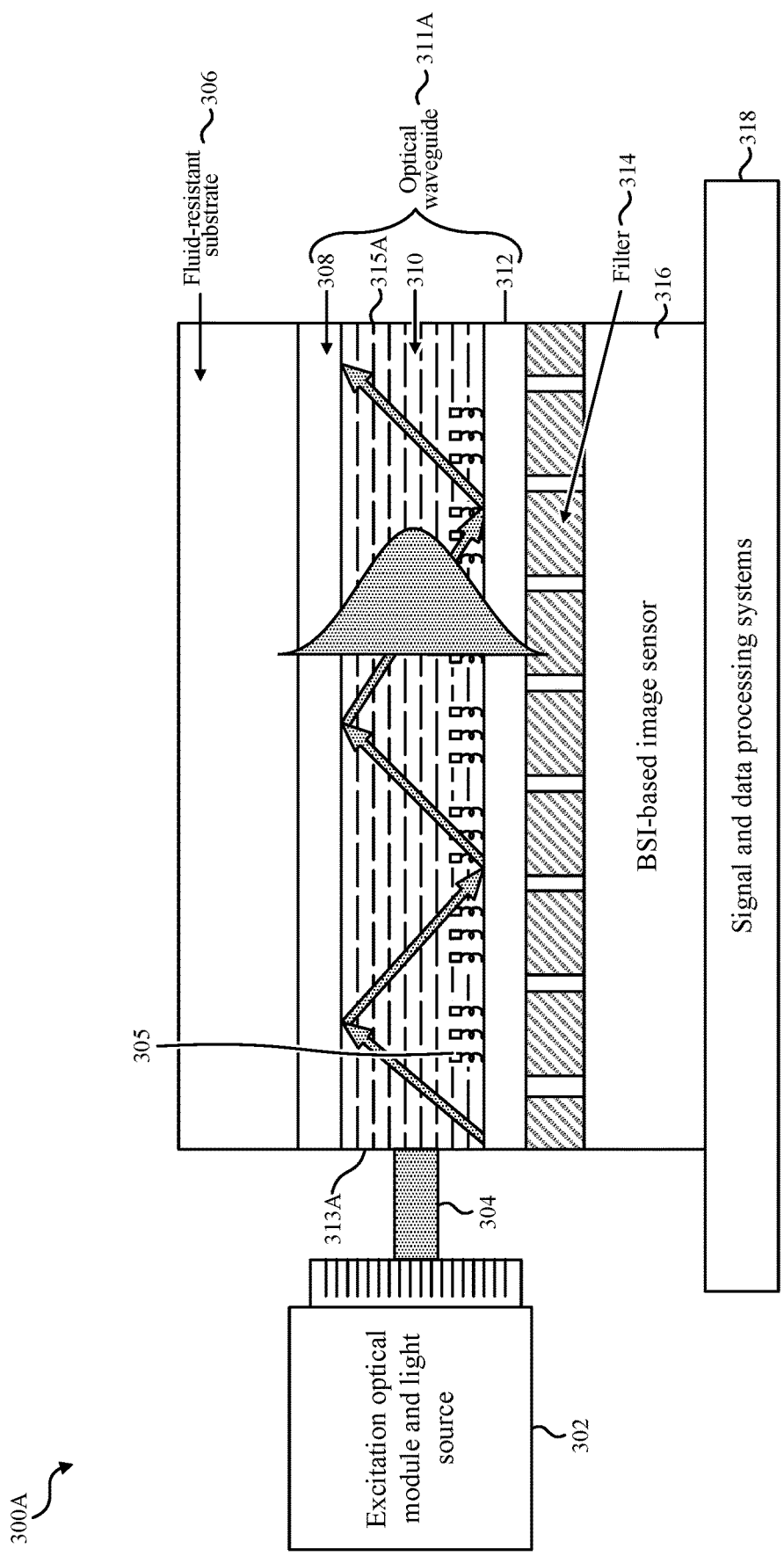
FIGS. 3A-3D illustrate different embodiments of exemplary liquid photonic systems of an analytical system.

As described above, in some embodiments, at least a portion of optical system 104, imaging system 106, and sensors 112 can be combined or integrated in a liquid photonic system. FIGS. 3A-3D illustrate different embodiments of exemplary liquid photonic systems 300A-D. As shown in FIG. 3A, a liquid photonic system 300A can include an excitation optical module and light source 302, a fluid-resistant substrate 306, an optical waveguide 311A, a filter 314, a BSI-based image sensor 316 (also referred to as image sensor 316), and signal and data processing systems 318.

With reference to FIG. 3A, in some embodiments, excitation optical module and light source 302 can include a laser or a light-emitting diode (LED) based light source that generates and emits an excitation light 304. Excitation light 304 can be, for example, a green light (e.g., a light having wavelength in the range of about 520-560 nm) or any other desired light having a desired wavelength or wavelength range. The light source that generates excitation light 304 can be, for example, a diode laser or LED. In some embodiments, excitation optical module and light source 302 can include further optical components such as beam shaping optics to form a uniform collimated line shape. As shown in FIG. 3A, excitation optical module and light source 302 can be optically coupled to a first end 313A of an optical waveguide 311A. For example, one or more of grating(s), mirror(s), prism(s), diffuser(s), and other optical coupling devices can be used to direct excitation light 304 from excitation optical module and light source 302 toward first end 313A of optical waveguide 311A. Excitation light 304 can be associated with a single wavelength, a plurality of wavelengths, or a wavelength range (e.g., wavelengths between 200 nm to 1600 nm).

As shown in FIG. 3A, excitation light 304 is directed toward first end 313 of optical waveguide 311A. In some embodiments, optical waveguide 311A can include three parts or three layers—a first light-guiding layer 308, a fluidic reaction channel 310, and a second light-guiding layer 312. Fluidic reaction channel 310 is bounded by first light-guiding layer 308 on one side (e.g., the top side) and bounded by second light-guiding layer 312 on the other side (e.g., the bottom side). Fluidic reaction channel 310 can be coupled to, for example, a first fluidic pipeline to receive and/or exchange liquid reagent from a multi-port rotary valve (e.g., valve 204 shown in FIG. 2). Fluidic reaction channel 310 can be further coupled to a second fluidic pipeline to deliver liquid reagent to the next fluidic reaction channel or a pump/waste container (e.g., pump 206 and waste container 208 shown in FIG. 2).

As illustrated in FIG. 3A, in some embodiments, a fluid-resistant substrate 306 can be disposed on top of optical waveguide 311A. Fluid-resistant substrate 306 can be a glass substrate, a plastic substrate, a polymer coated glass substrate, or any substrate that is fluid-resistant (e.g., water resistant, reagent resistant). In some embodiments, a first surface (e.g., the lower surface) of fluid-resistant substrate 306 is coated with first light-guiding layer 308. And fluidic reaction channel 310 is bounded on one side (e.g., the top side) by the first light-guiding layer 308 coated on fluid-resistant substrate 306. First light-guiding layer 308 can include, for example, at least one of a silicon dioxide layer, a silicon nitride, a polymer layer, or a dielectric layer. As described above, fluidic reaction channel 310 can be bounded on another side (e.g., the bottom side) by second light-guiding layer 312. Second light-guiding layer 312 can include, for example, at least one of a silicon dioxide layer, a silicon nitride, a polymer layer, or a dielectric layer.

With reference to FIG. 3A, first light-guiding layer 308 and second light-guiding layer 312 can form optical cladding layers of optical waveguide 311A (e.g., top cladding and bottom cladding, respectively). The liquid reagent included in fluidic reaction channel 310 can form an optical core layer of optical waveguide 311A. In an optical waveguide, the cladding layers have optical refractive indexes that are less than the optical core layer, such that the light travelling inside the optical core layer is substantially confined in the optical core layer by total internal reflection. As an example, the liquid reagent included in fluid reaction channel 310 may be water-based and have a refractive index of 1.34; while the first light-guiding layer 308 and second light-guiding layer 312 may have reflection index of 1.30. As a result, the excitation light 304 received at first end 313A of optical waveguide 311A is substantially confined inside fluidic reaction channel 310 while it is directed toward a second end 315A of optical waveguide 311A along the longitudinal direction of optical waveguide 311A. Confining the excitation light 304 inside the fluidic reaction channel 310 can improve the amount of light illumination or excitation of samples 305 (e.g., sequencing samples disposed on the surface of second light-guiding layer 312 inside fluidic reaction channel 310). In some embodiments, improving the amount of light illumination of excitation (e.g., increasing the intensity of light) can in turn enhance the signal strength of the light emitted from samples 305 as a result of the excitation. In contrast, conventional illumination techniques typically use top illumination or excitation where the excitation light is directed from the top of samples 305 (e.g., in a direction perpendicular to fluid-resistant substrate 306). The conventional illumination techniques thus have less signal strength due to the loss of excitation light (e.g., light is not confined and the light source may be far away from sample 305). As a result, comparing to the optical waveguide illumination techniques described in this application, conventional illumination techniques using top illumination typically do not provide a good signal-to-noise ratio and are thus less efficient.

As illustrated in FIG. 3A, in some embodiments, samples 305 can be disposed on the surface of second light-guiding layer 312. Second light-guiding layer 312 is disposed closer to image sensor 316 than first light-guiding layer 308. As a result, the photons of the light emitted from samples 305 as a result of the illumination or excitation travel a short distance (e.g., below 10 um) before they are detected by image sensor 316. The short distance photons required to travel further enhances the signal strength and reduces the loss of the light emitted from samples 305. Moreover, the reduced distance between optical waveguide 311A and image sensor 316 can reduce or eliminate the need for photon collection devices (e.g., a micro-lens array), which are often times complex and costly. Instead, near field optics can be used for transferring photons emitted from the samples to the image sensor without the need of additional optical path between them. After detecting photons of the light emitted from samples 305, image sensor 316 can convert the photons to electrical signals, which are then processed by signal and data processing systems 318. Image sensor 316 and signal and data processing systems 318 are described in more detail below.

Figure 3B:
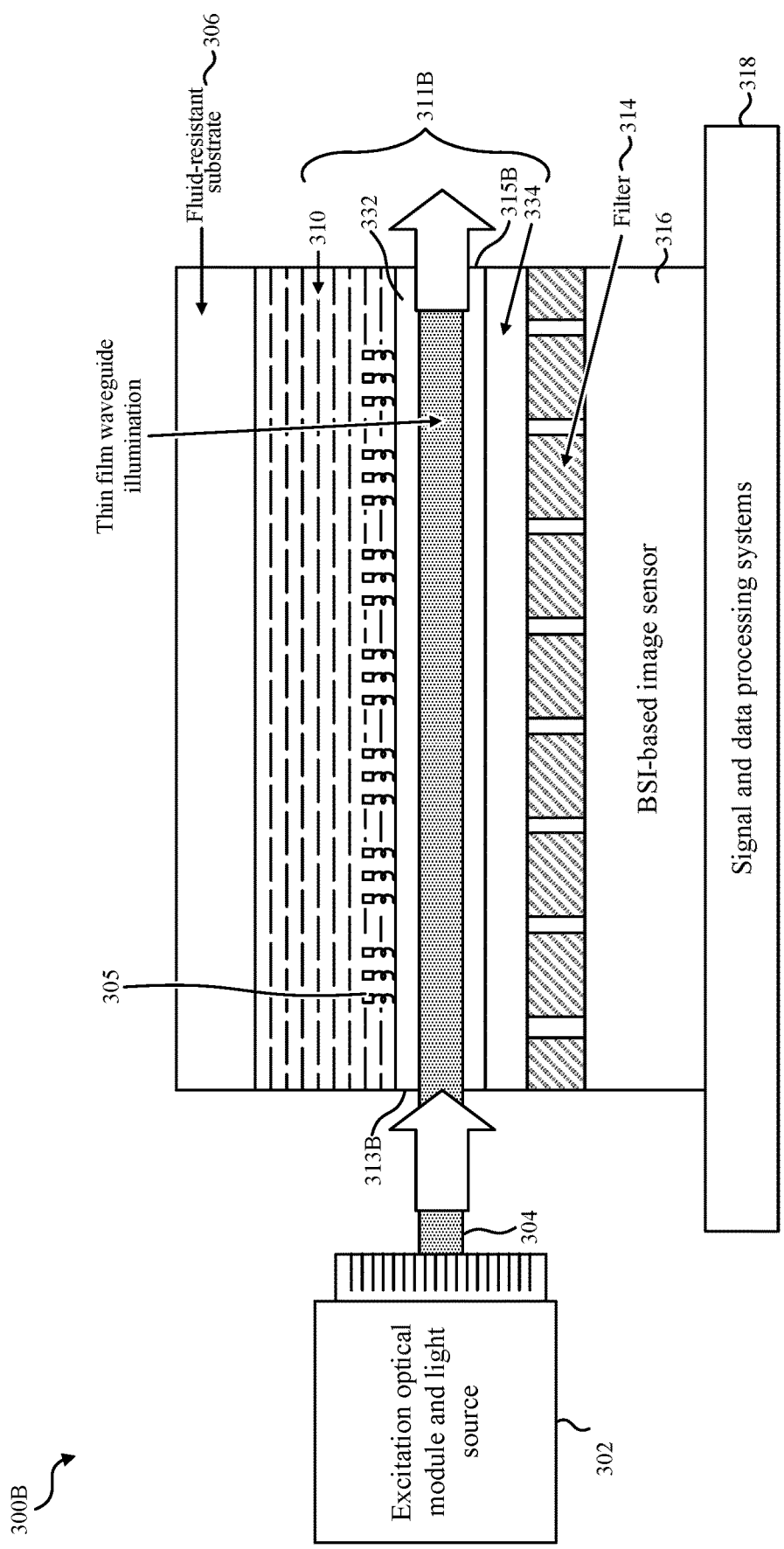

FIG. 3B illustrates a liquid photonic system 300B. With reference to FIG. 3B, similar to FIG. 3A, excitation light 304 can be generated and directed toward a first end 313B of optical waveguide 311B of liquid photonic system 300B. In the embodiment illustrated in FIG. 3B, optical waveguide 311B includes three parts or layers—a fluidic reaction channel 310, a first light-guiding layer 332, and a second light-guiding layer 334. As shown in FIG. 3B, fluidic reaction channel 310 is bounded by a fluid-resistant substrate 306 (e.g., a glass layer or a plastic sheet) on one side (e.g., the top side) and bounded by first light-guiding layer 332 on the other side (e.g., the bottom side). Fluidic reaction channel 310 can be coupled to, for example, a first fluidic pipeline to receive and/or exchange liquid reagent from a multi-port rotary valve (e.g., valve 204 shown in FIG. 2). Fluidic reaction channel 310 can be further coupled to a second fluidic pipeline to deliver liquid reagent to the next liquid photonic system or a pump/waste container (e.g., pump 206 and waste container 208 shown in FIG. 2).

As illustrated in FIG. 3B, in some embodiments, first light-guiding layer 332 can be a thin film waveguide layer configured to receive and direct excitation light 304. A thin film waveguide layer can include a core layer with optical transmission dielectric materials, for example, silicon nitride ($Si_xN_x$), Titanium dioxide ($TiO_2$), tantalum pentoxide ($Ta_2O_5$) layers and/or ceramic/polymer coatings with a refractive index (e.g., about 1.6-2) that is greater than the refractive index of a glass substrate or water. A thin film waveguide layer can have a thickness in the range of about tens of nanometers to tens of micrometers. In some embodiments, a thin film waveguide can be a plasmonic optical waveguide (e.g., a waveguide formed by the interface of a metal film based on the plasmonic effects) layer or a hybrid plasmonic waveguide (e.g., a waveguide formed by a combination of a dielectric layer and a plasmonic metal layer). A hybrid plasmonic waveguide can include, for example, a thin layer of (e.g., 50 nm) silicon dioxide ($SiO_2$) formed between a layer of silicon (e.g., a high refractive index silicon) and a metal surface (e.g., gold surface). A hybrid plasmonic waveguide can confine light or optical wave more tightly inside the waveguide, reduce leakage of light, and thus improve the power density and light propagation lost. A thin film waveguide layer can be deposited by using physical and/or chemical deposition methods, such as plasma-enhanced chemical vapor deposition (PECVD), metal organic chemical vapor deposition (MOCVD), ion sputtering, or the like. In some embodiments, to couple light into the thin film waveguide core layer efficiently, coupling gratings can be added to or integrated with a thin film waveguide layer by adding periodic structures under or above the thin film waveguide layer. In some embodiments, second light-guiding layer 334 can include, for example, at least one of a silicon dioxide layer, a silicon nitride, a polymer layer, or a dielectric layer.

With reference to FIG. 3B, in some embodiments, second light-guiding layer 312 and the liquid reagent included in fluidic reaction channel 310 can form optical cladding layers of optical waveguide 311B. First light-guiding layer 332 (e.g., a thin film waveguide layer) can form an optical core layer of optical waveguide 311B, such that light travelling in the first light-guiding layer 332 is substantially confined in the first light-guiding layer 332 by total internal reflection. As an example, first light-guiding layer 332 (e.g., the thin film waveguide layer) may have a refractive index of about 2.0. The liquid reagent included in fluid reaction channel 310 may be water-based and have a refractive index of 1.34; and the second light-guiding layer 312 may have a reflection index of 1.30. As a result, excitation light 304 received at first end 313B of optical waveguide 311B is substantially confined inside first light-guiding layer 332 while it is directed toward a second end 315B of optical waveguide 311B along the longitudinal direction of optical waveguide 311B. Confining the excitation light 304 inside first light-guiding layer 332 can increase the amount of light illumination or excitation of samples 305 (e.g., sequencing samples disposed on the surface the thin film waveguide layer inside the fluidic reaction channel 310).

In some embodiments, improving the amount of light illumination of excitation (e.g., increasing the intensity of light) can in turn enhance the signal strength of the light emitted from samples 305 as a result of the excitation. As described above, first light-guiding layer 332 may be a thin film waveguide layer (e.g., a layer having a thickness of 100 nm to 1 um). As a result, the intensity of the light confined in the thin film waveguide layer can be significantly increased and thus provide a further enhanced excitation, which in turn provides a further improved signal-to-noise ratio. In contrast, as described above, conventional illumination techniques using top illumination typically do not provide a good signal-to-noise ratio and are thus less efficient.

Moreover, a thin film waveguide can also reduce background noise by decreasing the penetration depth of an evanescence wave. An evanescence wave is generated by the photons of the excitation light. Therefore, by substantially confining the scatter light inside the waveguide, a thin film waveguide can reduce or prevent the scattering light from reaching the image sensor. This further improves the signal-to-noise ratio.

As illustrated in FIG. 3B, in some embodiments, samples 305 can be disposed on the surface of first light-guiding layer 332, which bounds fluidic reaction channel 310 on one side. First light-guiding layer 332 is disposed closer to image sensor 316 than fluid-resistant substrate 306. Thus, the photons of the light emitted from samples 305 as a result of the illumination or excitation travel a short distance (e.g., below about 10 um) before they are detected by image sensor 316. The short distance further enhances the signal strength and reduces the loss of the light emitted from samples 305. After detecting photons of the light emitted from samples 305, image sensor 316 can convert the photons to electrical signals, which are then processed by signal and data processing systems 318. Image sensor 316 and signal and data processing systems 318 are described in more detail below.

Figure 3C:
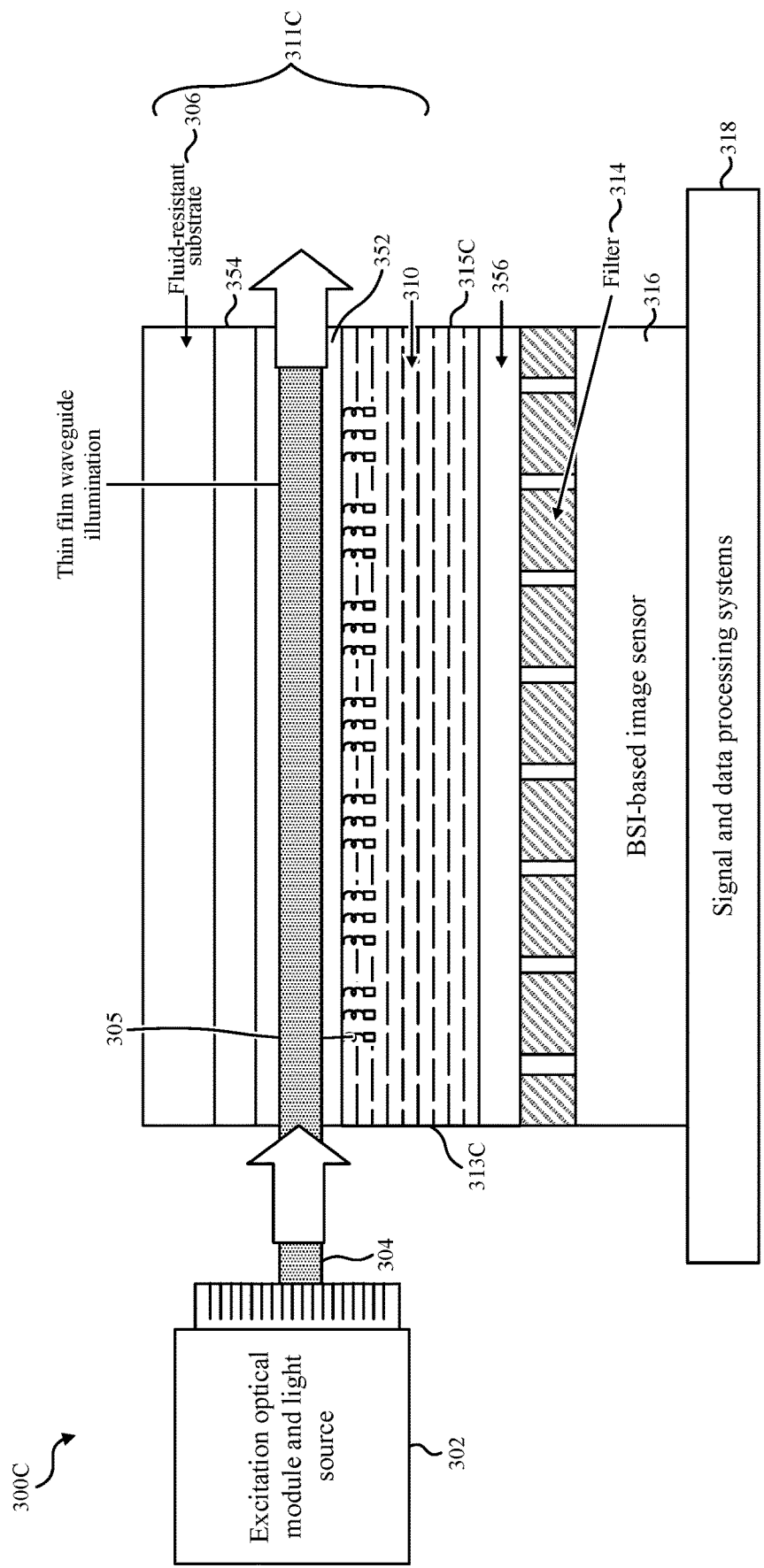

FIG. 3C illustrates a liquid photonic system 300C. With reference to FIG. 3C, similar to FIG. 3A, excitation light 304 can be generated and directed toward a first end 313C of optical waveguide 311C of liquid photonic system 300C. In the embodiment illustrated in FIG. 3C, optical waveguide 311C includes three parts or three layers—a fluidic reaction channel 310, a first light-guiding layer 352, and a second light-guiding layer 354. As shown in FIG. 3C, second light-guiding layer 354 can be coated on a surface of a fluid-resistant substrate 306 (e.g., a glass layer or a plastic sheet); and second light-guiding layer 354 can be disposed between fluid-resistant substrate 306 and first light-guiding layer 352. Fluidic reaction channel 310 is bounded by first light-guiding layer 352 on one side (e.g., the top side) and bounded by a second fluid-resistant substrate 356 (e.g., a glass substrate or a plastic sheet) on the other side (e.g., the bottom side). Fluidic reaction channel 310 can be coupled to, for example, a first fluidic pipeline to receive and/or exchange liquid reagent from a multi-port rotary valve (e.g., valve 204 shown in FIG. 2). Fluidic reaction channel 310 can be further coupled to a second fluidic pipeline to deliver liquid reagent to the next liquid photonic system or a pump/waste container (e.g., pump 206 and waste container 208 shown in FIG. 2).

As illustrated in FIG. 3C, in some embodiments, similar to first light-guiding layer 332 shown in FIG. 3B, first light-guiding layer 352 can be a thin film waveguide layer configured to receive and direct excitation light 304. First light-guiding layer 352 is thus not repeatedly described. Second light-guiding layer 354 can include, for example, at least one of a silicon dioxide layer, a silicon nitride, a polymer layer, or a dielectric layer. Second light-guiding layer 354 can be similar to second light-guiding layer 334 described above with respect to FIG. 3B, and thus not repeatedly described.

With reference to FIG. 3C, in some embodiments, second light-guiding layer 354 and the liquid reagent included in fluidic reaction channel 310 can form optical cladding layers of optical waveguide 311C. First light-guiding layer 352 (e.g., a thin film waveguide layer) can form optical core layer of optical waveguide 311C, such that light travelling in first light-guiding layer 352 is substantially confined in first light-guiding layer 352 by total internal reflection. As an example, first light-guiding layer 352 (e.g., the thin film waveguide layer) may have a refractive index of about 2.0). The liquid reagent included in fluid reaction channel 310 may be water-based and have a refractive index of 1.34; and the second light-guiding layer 354 may have a reflection index of 1.45. As a result, excitation light 304 received at a first end 313C of optical waveguide 311C is substantially confined inside first light-guiding layer 352 while it is directed toward a second end 315C of optical waveguide 311C along the longitudinal direction of optical waveguide 311C.

Confining excitation light 304 inside first light-guiding layer 352 (e.g., a thin film waveguide layer) can increase the amount of light illumination or excitation of samples 305 (e.g., sequencing samples disposed on a surface of the thin film waveguide layer inside the fluidic reaction channel 310). In some embodiments, improving the amount of light illumination of excitation (e.g., increasing the intensity of light) can in turn enhance the signal strength of the light emitted from samples 305 as a result of the excitation. As described above, first light-guiding layer 352 may be a thin film waveguide layer having a thickness of 100 nm to 1 um. As a result, the intensity of the light confined in the thin film waveguide layer can be significantly increased and thus provide a further enhanced excitation, which in turn further improves the signal-to-noise ratio. In contrast, as described above, conventional illumination techniques using top illumination or excitation typically do not provide a good signal-to-noise ratio and are thus less efficient.

Moreover, a thin film waveguide can also reduce background noise by decreasing the penetration depth of an evanescence wave. An evanescence wave is generated by the photons of the excitation light. Therefore, by substantially confining the scatter light inside the waveguide, a thin film waveguide can reduce or prevent the scattering light from reaching the image sensor. This further improves the signal-to-noise ratio.

As illustrated in FIG. 3C, in some embodiments, for receiving excitation light 304, samples 305 can be disposed on a surface of first light-guiding layer 352, which bounds fluidic reaction channel 310 on one side. In this embodiment, first light-guiding layer 352 is disposed further away from image sensor 316 than second fluid-resistant substrate 356, which bounds the other side of fluidic reaction channel 310. In some embodiments, to reduce the distance that the photons of the light emitted from samples 305 must travel before they can be detected by image sensor 316, an actuator (not shown) can be coupled to the optical waveguide 311C (e.g., through fluid-resistant substrate 306). The actuator can be electrically, pneumatically, or hydraulically powered to adjust the thickness of the fluidic reaction channel 310 (e.g., by applying a force perpendicular to fluidic reaction channel 310 through fluid-resistant substrate 306) in accordance with different operating modes of the liquid photonic system 300C. For example, when the liquid photonic system 300C is controlled to receive liquid reagent, the actuator may not apply force to fluidic reaction channel 310 such that the thickness (e.g., the vertical height) of fluidic reaction channel 310 is at its maximum. When the liquid photonic system 300C is controlled to provide excitation light 304 to samples 305 (e.g., illuminating samples 305 for sequencing testing), the actuator may apply a predetermined force to fluidic reaction channel 310 such that the thickness (e.g., the vertical height) of fluidic reaction channel 310 is reduced. As a result, the distance that the photons of light emitted from samples 305 need to travel to reach image sensor 316 is also reduced (e.g., reduced to about 1-10 um from about 50-100 um). This enhances the signal strength and reduces the loss of the light emitted from samples 305.

In some embodiments, liquid photonic system 300C can further include a pressure sensor (not shown) configured to sense a pressure applied on fluidic reaction channel 310 by the actuator. Based on the sensed pressure, the pressure sensor can provide a feedback signal to the actuator and/or a control system (e.g., control system 110 shown in FIG. 1). Based on the feedback signal, the amount of force applied by the actuator can be adjusted or maintained in accordance with a desired thickness (e.g., vertical height) of the fluidic reaction channel 310. After detecting photons of the light emitted from samples 305, image sensor 316 can convert the photons to electrical signals, which are then processed by signal and data processing systems 318. Image sensor 316 and signal and data processing systems 318 are described in more detail below.

Figure 3D:
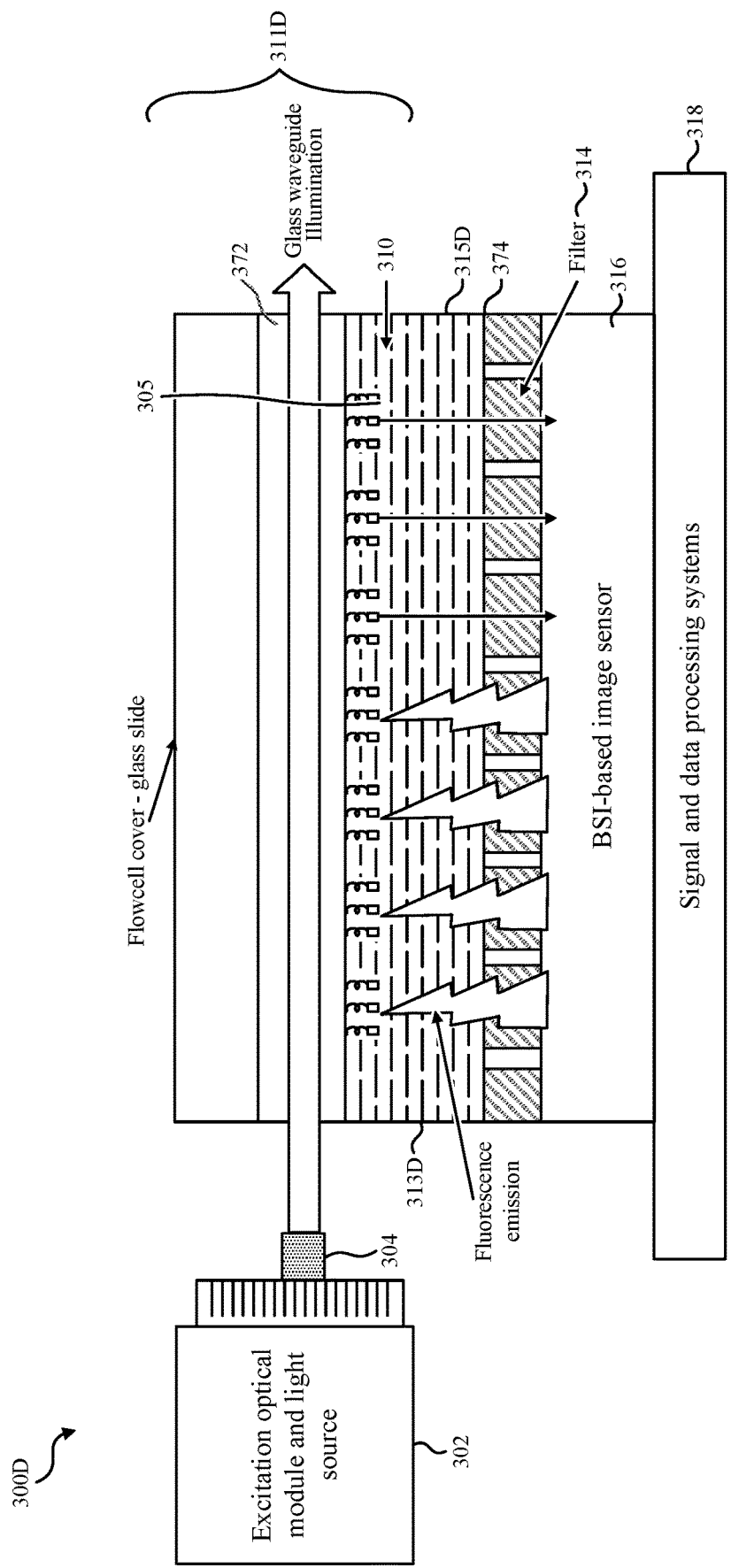

FIG. 3D illustrates a liquid photonic system 300D. With reference to FIG. 3D, similar to FIG. 3A, excitation light 304 can be generated and directed toward optical waveguide 311D of liquid photonic system 300D. In the embodiment illustrated in FIG. 3D, optical waveguide 311D includes two parts or two layers—a fluidic reaction channel 310 and a first light-guiding layer 372. As shown in FIG. 3D, in some embodiments, first light-guiding layer 372 can include a fluid-resistant substrate (e.g., a glass layer or a plastic sheet). Fluidic reaction channel 310 is bounded by first light-guiding layer 372 on one side (e.g., the top side) and bounded by a second fluid-resistant substrate 374 (e.g., a glass substrate or a plastic sheet) on the other side (e.g., the bottom side). Fluidic reaction channel 310 can be coupled to, for example, a first fluidic pipeline to receive and/or exchange liquid reagent from a multi-port rotary valve (e.g., valve 204 shown in FIG. 2). Fluidic reaction channel 310 can be further coupled to a second fluidic pipeline to deliver liquid reagent to the next liquid photonic system or a pump/waste container (e.g., pump 206 and waste container 208 shown in FIG. 2).

As illustrated in FIG. 3D, in some embodiments, first light-guiding layer 372 can be a glass substrate configured to receive and direct excitation light 304. In some embodiments, first light-guiding layer 372 forms the optical core layer (e.g., for glass waveguide illumination) of optical waveguide 311D. A gas (e.g., air) filled within a chamber (not shown) housing at least a part of the optical waveguide 311D and/or other components of liquid photonic system 300D can form an optical cladding layer (e.g., the top cladding layer); while the liquid reagent included in fluidic reaction channel 310 can form another optical cladding layer (e.g., bottom cladding layer) of optical waveguide 311D. In an optical waveguide, as discussed above, the cladding layers have optical refractive indexes that are less than the optical core layer, such that light travelling in the optical core layer is substantially confined in the optical core layer by total internal reflection. As an example, first light-guiding layer 372 (e.g., the glass waveguide) can have a refractive index of about 1.45-1.57. The liquid reagent included in fluid reaction channel 310 may be water-based (or any other aqueous solution or oil-based) and have a refractive index of 1.34; and the gas (e.g., air) filled within the chamber at least partially housing the optical waveguide 311D may have a reflection index of 1.0. As a result, the excitation light 304 received at a first end 313D of optical waveguide 311D is substantially confined inside first light-guiding layer 372 (e.g., the glass waveguide) while it is directed toward a second end 315D of optical waveguide 311D along the longitudinal direction of optical waveguide 311D. Confining the excitation light 304 inside first light-guiding layer 372 can increase the amount of light illumination or excitation of samples 305 (e.g., sequencing samples) disposed on a surface of first light-guiding layer 372 inside the fluidic reaction channel 310. In some embodiments, improving the amount of light illumination of excitation (e.g., increasing the intensity of light) can in turn enhance the signal strength of the light emitted from samples 305 as a result of the excitation. As described above, first light-guiding layer 372 may include a glass waveguide having a thickness of 50-200 um. As a result, the light signal intensity confined in the glass waveguide can be significantly increased and thus provide a further enhanced excitation. In contrast, as described above, conventional illumination techniques using top illumination or excitation typically do not provide a good signal-to-noise ratio and are thus less efficient.

As illustrated in FIG. 3D, in some embodiments, for receiving excitation light 304, samples 305 can be disposed on a surface (e.g., bottom surface) of first light-guiding layer 372, which bounds fluidic reaction channel 310 on one side. In this embodiment, first light-guiding layer 372 is disposed further away from image sensor 316 than second fluid-resistant substrate 374, which bounds the other side of fluidic reaction channel 310. In some embodiments, to reduce the distance that the photons of the light emitted from samples 305 must travel before they can be detected by image sensor 316, an actuator (not shown) can be coupled to the optical waveguide 311D. The actuator can be electrically, pneumatically, or hydraulically powered to adjust the thickness (e.g., vertical height) of the fluidic reaction channel 310 (e.g., by applying a force perpendicular to fluidic reaction channel 310 through fluid-resistant substrate 306) in accordance with different operating modes of the liquid photonic system 300D. In some embodiments, liquid photonic system 300D can further include a pressure sensor (not shown) configured to sense a pressure applied on the fluidic reaction channel 310 by the actuator; and provide a feedback signal to the actuator and/or a control system (e.g., control system 110 shown in FIG. 1). The actuator and pressure sensor are similar to those described above and thus not repeatedly described.

Each of the liquid photonic systems 300A-D described above includes an optical waveguide 311A-D, respectively. An optical waveguide (e.g., 311A-D) allows the continuous propagation of photons with low loss (e.g., less than about 1-10% loss) over a long distance (e.g., about 10 centimeters). As illustrated above in FIGS. 3A-3D, some of the optical waveguides 311A-D direct light in or near a fluidic reaction channel 310; and some of the optical waveguides 311A-D direct light near or along the surface of image sensor 316. The continuous propagation of photons along or near the surface of an image sensor and/or in or near the fluidic reaction channel can provide at least two benefits. First, the optical waveguide configurations illustrated above can provide continuous excitation to a plurality of samples (e.g., DNA molecules) at different locations inside the fluidic reaction channel, by a single light or photonic wave with a high optical power density (e.g., about 1-10 $kW/cm^2$) and/or by a light source at low power (e.g., 10-100 mW) with reduced cost. Second, the optical waveguide configurations illustrated above can guide photons of the excitation light away from the image sensor to reduce background noise or leakage, which can be beneficial or critical for fluorescence imaging. For example, the optical waveguide configurations illustrated above can effectively reduce background noise two to three fold compared with conventional top illumination (e.g., the excitation light illuminates the samples from the top in a perpendicular direction to the fluidic reaction channel) configurations that do not use optical waveguide. The optical waveguide configurations illustrated above thus not only greatly improve the detection sensitivity but also reduce the requirements of color filter for filtering the excitation light (e.g., reduces the filtering requirements by about 2-3 fold). As a result, the requirement of a high-performing color filter can be relaxed, enabling the using of a standard color filter (e.g., a less expensive medium performance filter) for florescence detection by a CMOS image sensor. In contrast, using a non-standard color filter in either material or fabrication process can easily result in incurring additional development cost over millions of dollars, delaying of product delivery in years, and/or losing the access of high-quality foundries with advanced technologies.

Figure 4A:
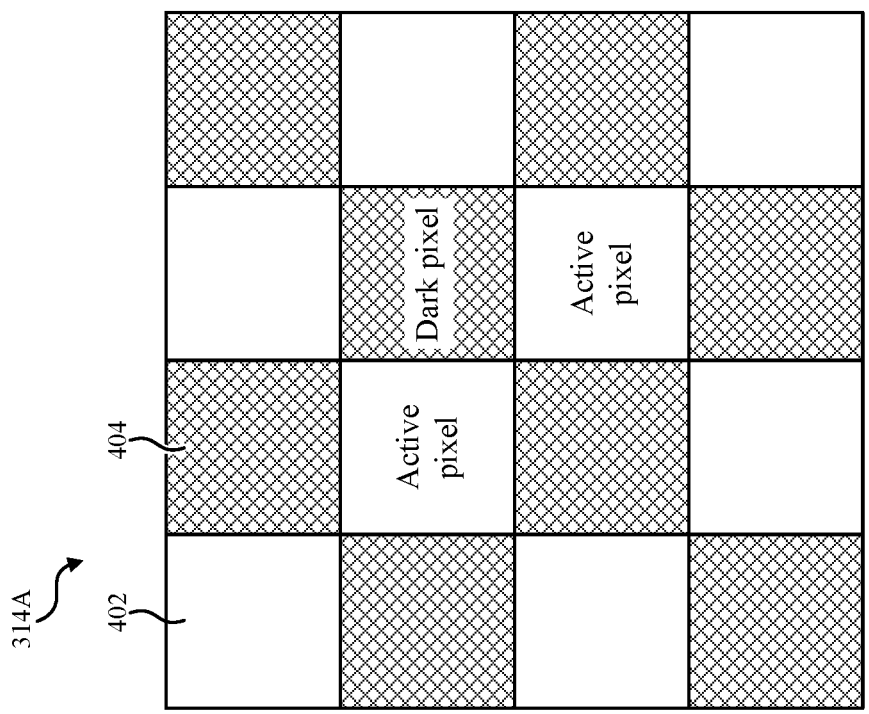
FIG. 4A illustrates a top view and a cross-sectional view of an embodiment of an exemplary filter of an analytical system.
Figure 4A:
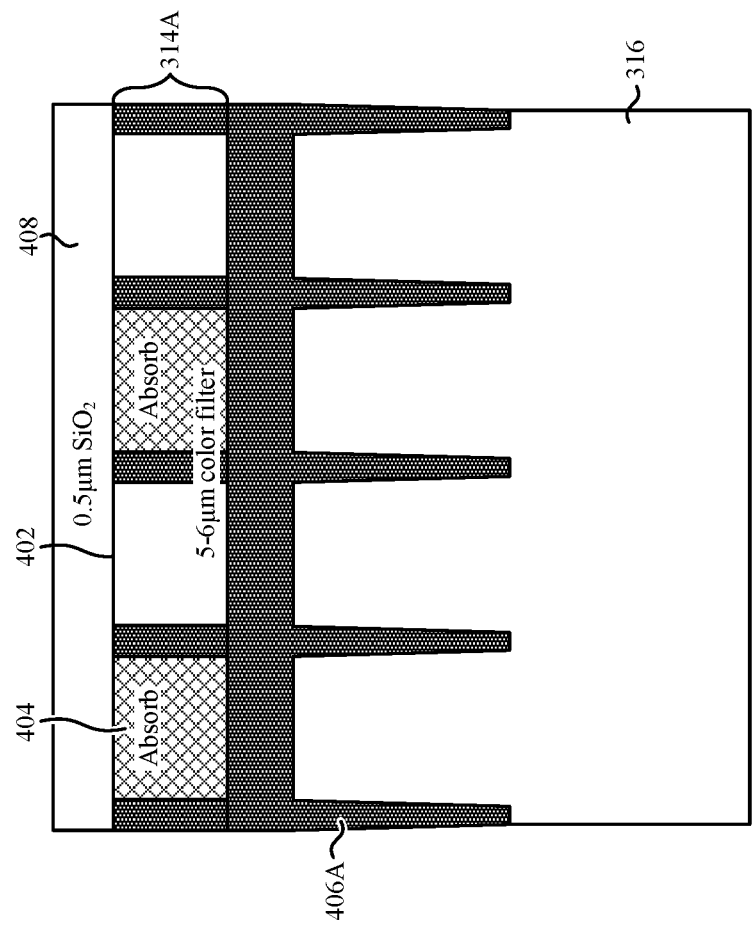

In the embodiments shown in FIGS. 3A-3D, one or more of liquid photonic systems 300A-D can optionally include a filter 314 disposed between optical waveguide 311A-D, respectively, and image sensor 316. FIG. 4A illustrates a top view and a cross-sectional view of such a filter 314A. As shown in the top view of FIG. 4A (left side of FIG. 4A), in some embodiments, filter 314A can include a plurality of filter cells 402 and 404. Filter cells 402 can be of a first-type filter cells configured to remove a substantial portion of light having a first wavelength range; and filter cells 404 can be a second-type filter cells configured to remove a substantial portion of light having a second wavelength range. For example, filter cells 402 can be a coating deposited on image sensor 316 for removing a substantial portion of scattered or leakage light in the wavelength range of the excitation light (e.g., green light); while allowing a substantial portion of the light emitted from the samples to pass (e.g., yellow light and/or red light). Thus, filter cells 402 can improve the signal-to-noise ratio by allowing desired light signals to reach image sensor 316 while blocking undesired light signals (e.g., background noise and/or excitation light leakage). In some embodiments, filter cells 404 can be a different type of coating deposited on image sensor 316 such that filter cells 402 and 404 are interleaved (e.g., forming a chessboard pattern separating different types of cells by a grid structure 406A) to reduce crosstalk between adjacent photosensitive elements (e.g., adjacent pixels) of the image sensor 316. Crosstalk is often undesired because the light emitted from one sample can be affected by the light emitted from another sample, resulting in signal distortion for some photosensitive elements (e.g., pixels) of an image sensor. Filter cells 404 can remove, for example, a substantial portion of all lights (e.g., absorb lights in all wavelength ranges or any desired wavelength ranges). Thus, by interleaving filter cells 404 with filter cells 402, crosstalk can be reduced or eliminated.

The cross-sectional view of filter 314A in FIG. 4A (right side of FIG. 4A) further illustrates the interleaving pattern of filter cells 402 and filter cells 404 to reduce crosstalk. In some embodiments, filter 314A may be an absorption polymer filter deposited on image sensor 316. Filter 314A can have, for example, a thickness of about 5-6 um. In some embodiments, filter 314A can be covered with a protection layer 408 deposited on top of the filter cells 402 and 404. Protection layer 408 can be a layer of, for example, silicon dioxide with a desired thickness (e.g., about 0.5 um). Protection layer 408 can protect filter cells from damages (e.g., chemical or mechanical damages) while allowing light to reach filter cells 402 and 404.

Figure 4B:
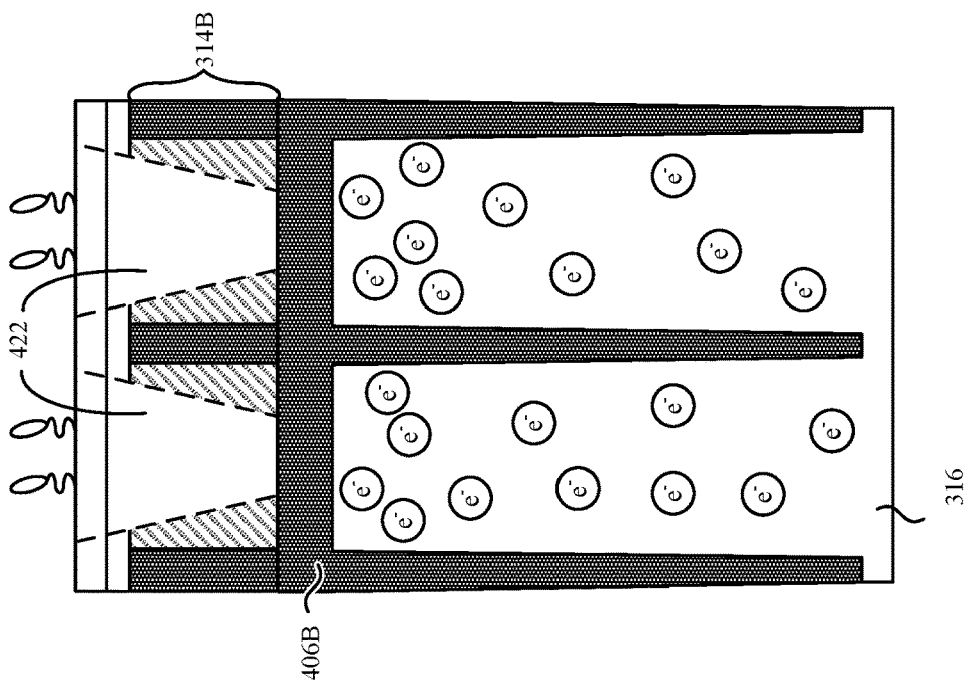
FIG. 4B illustrates cross-sectional views of another embodiment of an exemplary filter of an analytical system.
Figure 4B:
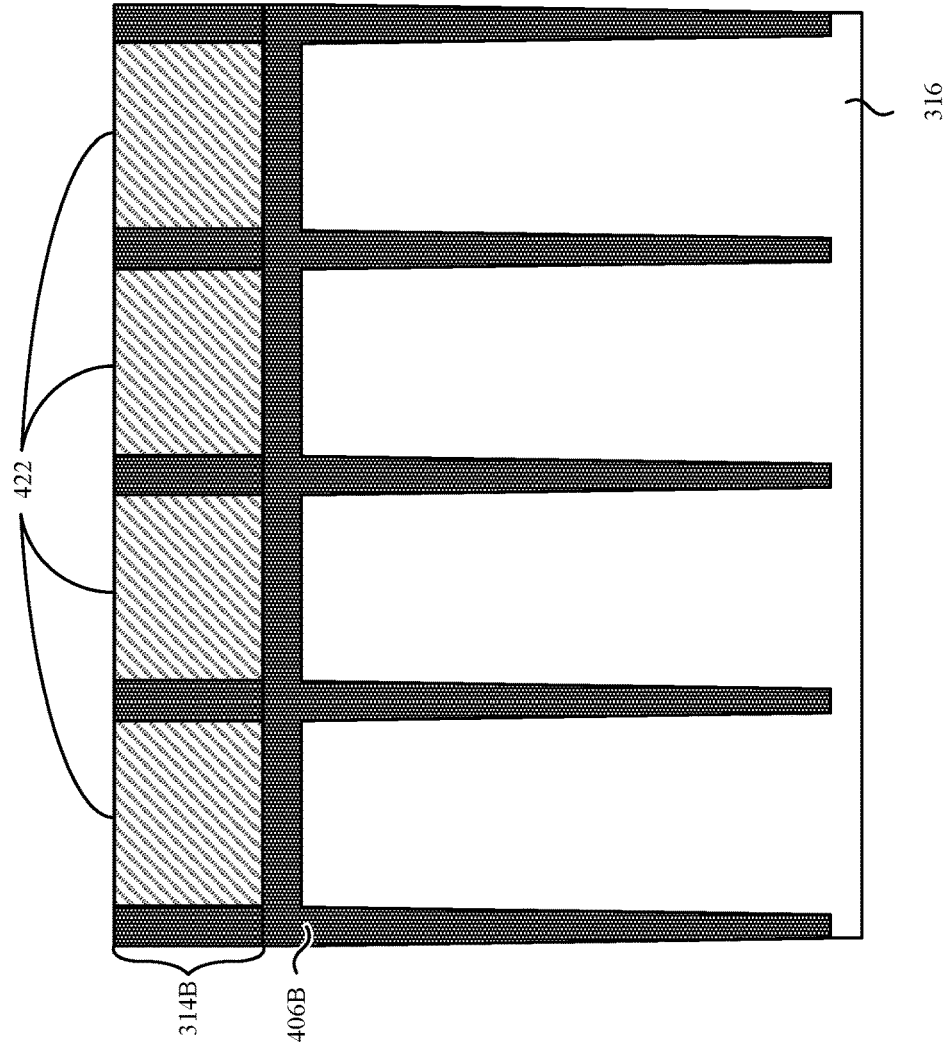

FIG. 4B illustrates cross sectional views of a different type of filter 314B. In this embodiment, filter 314B can include filter cells 422 similar to filter cells 402 of filter 314A shown in FIG. 4A. For example, similar to those in FIG. 4A, filter cells 422 can be a coating deposited on image sensor 316 for removing a substantial portion of scattered or leakage light in the wavelength range of the excitation light (e.g., green light); while allowing a substantial portion of the light emitted from the samples to pass (e.g., yellow light and/or red light). Unlike filter 314A, filter 314B shown in FIG. 4B does not include a second-type filter cell configured to remove a substantial portion of light having a wavelength range different from that of a first-type filter cell. Instead, filter 304B can include a monolayer (e.g., an absorption polymer layer) of coating on image sensor 316. The monolayer of coating forms filter cells 422. To reduce crosstalk, filter 314B can include a grid structure 406B separating adjacent filter cells 422. Compared to grid structure 406A as shown in FIG. 4A, grid structure 406B can have a larger depth such that it extends deeper into image sensor 316. As shown in FIG. 4B, a deeper grid structure reduces or eliminates crosstalk between adjacent photosensitive elements (e.g., pixels) of image sensor 316. In some embodiments, the depth of the grid structure 406B can be, for example, about 1-5 um. In some embodiments, grid structures 406A (shown in FIG. 4A) and 406B (shown in FIG. 4B) can be metal grids deposited on image sensor 316.

Figure 5A:
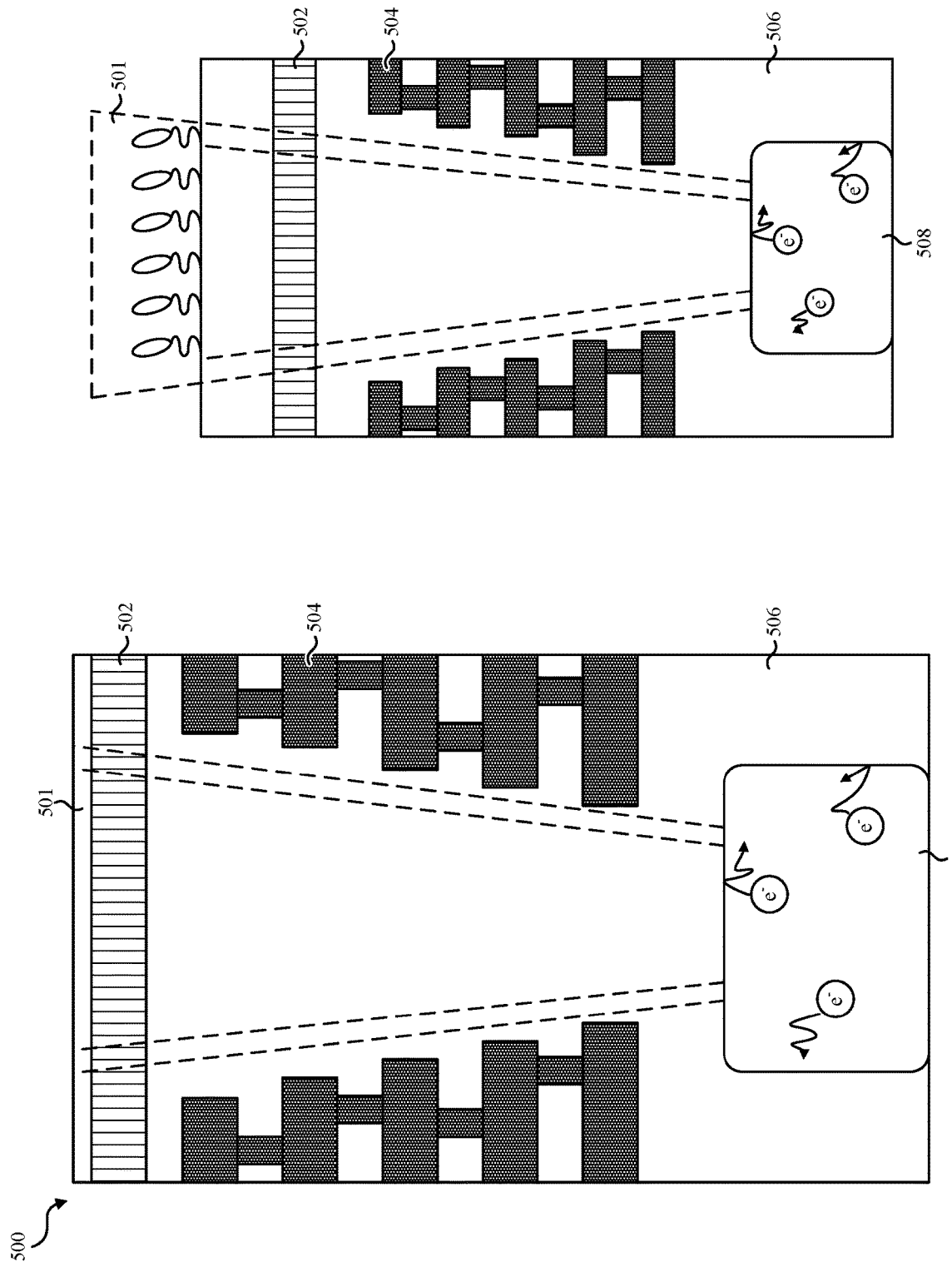
FIG. 5A illustrates a conventional front-side illumination (FSI) based CMOS image sensor of an analytical system.

As discussed above, each of liquid photonic systems 300A-D illustrated in FIGS. 3A-3D includes an image sensor 316. In some embodiments, image sensor 316 can be a backside illumination (BSI) based image sensor instead of a front side illumination (FSI) based image sensor. FSI-based image sensors are frequently used in conventional image sensing systems. FIG. 5A illustrates such a conventional FSI-based CMOS image sensor 500. As shown in FIG. 5A, image sensor 500 typically includes a passivation layer 502, a plurality of metal layers 504, a semiconductor substrate 506, and photosensitive elements 508. When image sensor 500 senses light 501, photons of light 501 need to travel through passivation layer 502 and an opening of the plurality of metal layers 504 before reaching photosensitive elements 508. Thus, the distance that light 501 needs to travel may sometimes be large. For example, modern integrated circuits and semiconductor-based image sensors (e.g., silicon-based CMOS sensor) may have multiple metal layers (e.g., 6-9 metal layers) stack on top of one another with dielectrics filled in between adjacent metal layers. The total distance of the metal layers can be, for example, about 5 um. The longer the distance light 501 needs to travel to photosensitive elements 508, the greater the loss of the signal strength.

Additionally, in an FSI-based image sensor, each photosensitive element (e.g., pixel) may require a signal readout and conversion circuitry that is implemented by multiple metal layers. Thus, because the layout areas are occupied by the multiple metal layers, only a small portion of each photosensitive element (e.g., pixel) may have access or be sensitive to light 501. Under some circumstances, the photosensitive area may be reduced by 30-40% due to the multiple metal layers implementing the signal readout and conversion circuitry. Reducing the photosensitive area further reduces the signal strength or limits the light absorption (characterized by quantum efficiency) of the image sensor. A reduced signal strength in turn reduces the image quality and requires a high-sensitivity image sensor, which can be expensive and sometime impractical. In certain low light applications, the FSI-based image sensor may not even have sufficient light to generate electrical signals. Further, to allow light 501 to pass through the multiple metal layers 504, an opening needs to be formed in the metal layers 504. This not only reduces the effective useful area of the metal layers, but also adds further complexity to the manufacturing process. Thus, an FSI-based image sensor often has low efficiency and low image quality due to the signal loss and can be associated with high cost.

Figure 5B:
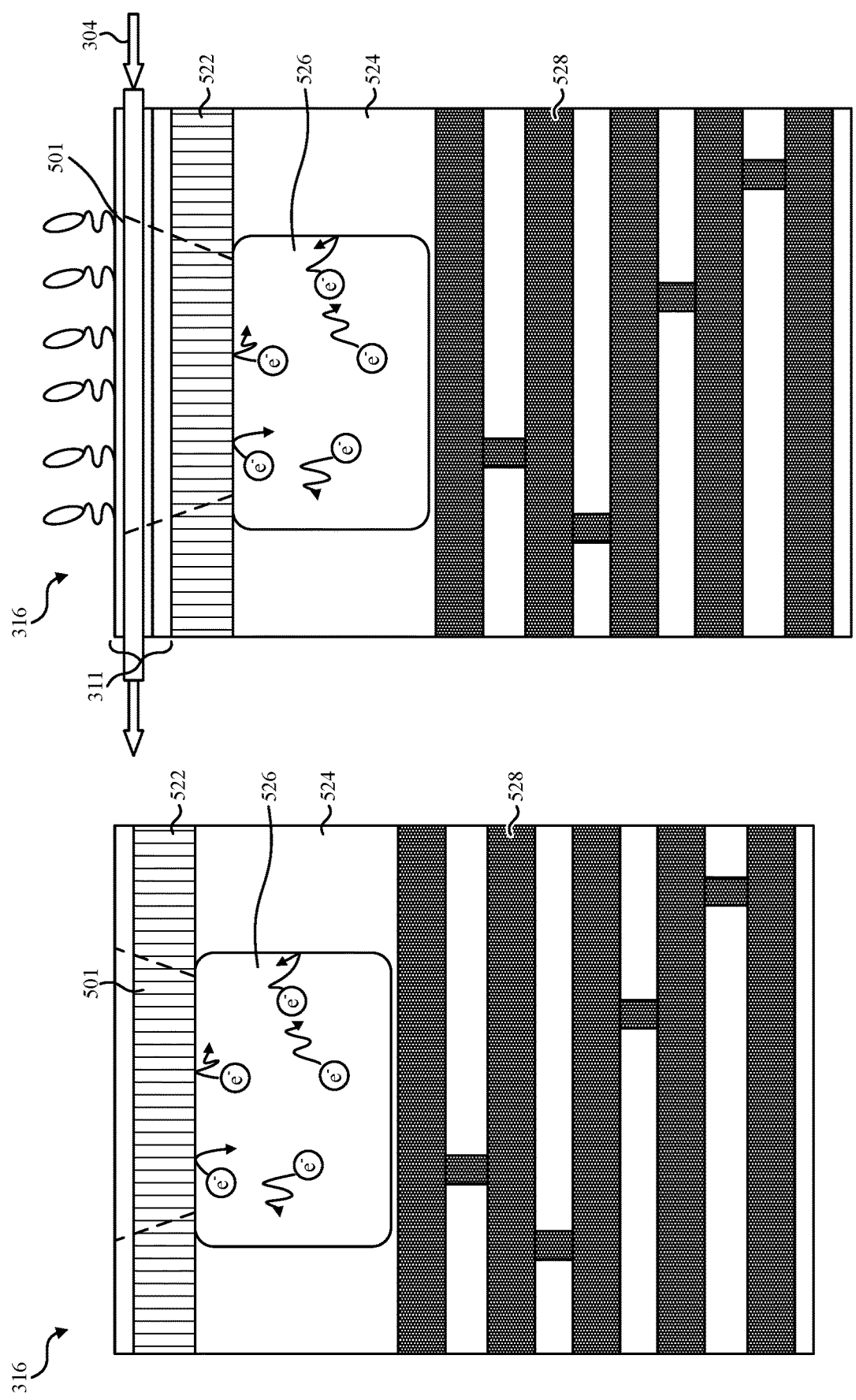
FIG. 5B illustrates an exemplary back-side illumination (BSI) based CMOS image sensor of an analytical system.

FIG. 5B illustrates an exemplary back-side illumination (BSI) based CMOS image sensor 316 used in liquid photonic systems 300A-D discussed above. In some embodiments, image sensor 316 includes a passivation layer 522, a semiconductor substrate 524, photosensitive elements 526, and a plurality of metal layers 528. In some embodiments, passivation layer 522 can be a polymer coating with low refractive index or a silicon dioxide layer. Semiconductor substrate 524 can be a silicon-based substrate. Unlike the FSI-based image sensor, BSI-based image sensor 316 receives light (e.g., the emitted light from samples being tested) from the back side of the image sensor. As illustrated in FIG. 5B, the backside of image sensor 316 can be coupled to an optical waveguide 311 (e.g., a thin film waveguide), such that light 501 can be received through the backside. For example, light 501 (e.g., light emitted from the samples disposed inside a fluidic reaction channel of optical waveguide 311 as a result of excitation by light 304) can be received at photosensitive elements 526 after traveling a short distance (e.g., about 0.5-2 um) through the passivation layer 522, without having to travel through any of metal layers 528.

In some embodiments, photosensitive elements 526 include, for example, photodiodes (e.g., silicon based photodiodes) and amplifiers, for detecting photons and generating electrical signals based on detected photons. The electrical signals can then be collected and conducted by the plurality of metal layers 528 that implement a signal readout and conversion circuitry. A BSI-based image sensor thus eliminates the need for light 501 to travel through the distance of the multiple metal layers 528, thus greatly reduces the signal loss and cross talk due to the distance of traveling. The short distance of travel also eliminates or reduces the need for additional fluorescence collection optics. Further, by eliminating the multiple metal layers in the light path, a substantial or entire area of photosensitive elements 526 can have access or be sensitive to light 501. A BSI-based image sensor thus significantly improves light absorption over an FSI-based image sensor. In some embodiments, the quantum efficiency of a BSI-based image sensor can be improved by 80-90% compared to an FSI-based image sensor. As discussed above, reducing signal loss and having higher quantum efficiency in turn improves image quality and resolution, and reduces the need for a highly-sensitive image sensor.

Further, using a BSI-based image sensor 316, there is no need to form an opening in the multiple metal layers 528, because light 501 is received from the backside of the image sensor. A BSI-based image sensor 316 thus effectively increases the useful metal area and reduces the manufacturing cost. For example, due to the eliminating of the metal layers in the light path, a BSI-based image sensor 316 can have a flatter and smoother surface (e.g., the surface of semiconductor substrate 524), which improves the surface compatibility between the image sensor 316 and the optical waveguide 311. Typically, a thin-film based optical waveguide (e.g., optical waveguide 311C) may include a layer of dielectric at the thickness of about 100 nm to 1 um. The light propagation and attenuation control of the optical waveguide rely on the flatness and smoothness of the thin film layer. A BSI-based image sensor can have a surface (e.g., a polished silicon surface) that has a high degree of flatness and smoothness. Thus, disposing or integrating the optical waveguide (e.g., a thin-film based optical waveguide) on top of a BSI-based image sensor can readily be performed due to the improved surface compatibility between the image sensor and the optical waveguide.

Figure 6:
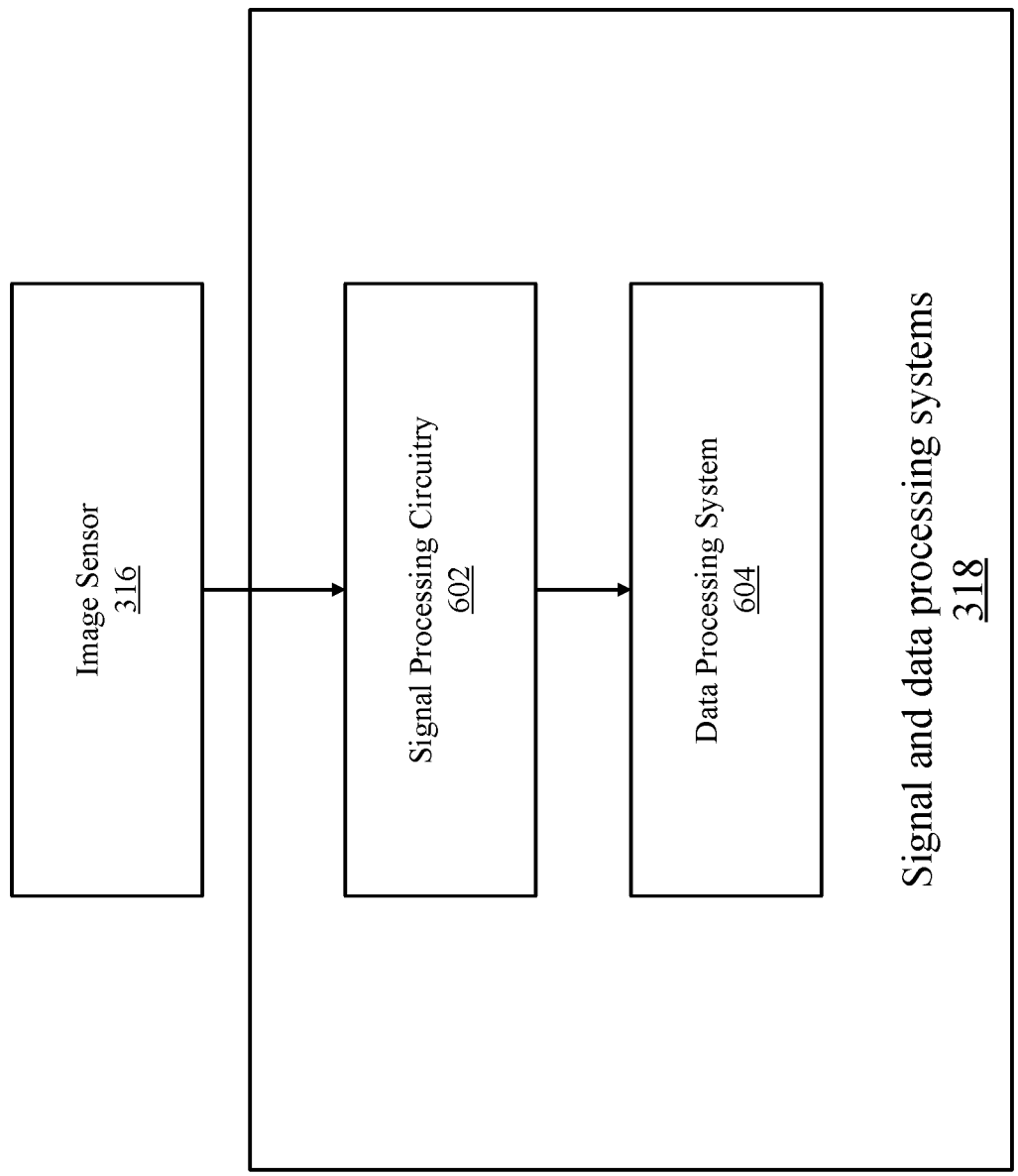
FIG. 6 illustrates an exemplary signal and data processing systems of an analytical system.

As discussed above, liquid photonic systems 300A-D shown in FIGS. 3A-3D can include signal and data processing systems 318. FIG. 6 illustrates exemplary signal and data processing systems 318, which can include a signal processing circuitry 602 and a data processing system 604. As discussed above, image sensor 316 can convert photons emitted from the samples to electrical signals. In some embodiments, image sensor 316 can be a large scale BSI-based image sensor with pixel readout of about 10 meg-1000 meg or higher. A large scale image sensor can provide high image sensing throughput because it can perform parallel light sensing in connection with high speed signal readout using global shutter technologies. In some embodiments, if image sensor 316 is a large scale BSI-based image sensor, it may require a correspondingly large area on a semiconductor die or chip, which frequently also includes other circuitries such as a signal readout circuitry. This in turn may require an increase of the size of a semiconductor die or chip, and thus making manufacturing process challenging. In some embodiments, the photosensitive elements of BSI-based image sensor 316 can be formed in a first semiconductor die (also referred to as a sensor die/wafer), while the associated signal processing circuitry 602 (e.g., readout circuitry for processing signals generated from photosensitive elements) can be formed in a second semiconductor die (also referred to as a readout die/wafer). In some embodiments, the first and second semiconductor dies can be stacked or overlaid to reduce chip area. For example, because image sensor 316 in the first die is a BSI-based sensor with metal layers facing down, the signal readout circuitry in the second die can thus have metal layers facing up to electrically interconnect with image sensor 316 for receiving the electrical signals generated by image sensor 316.

As shown in FIG. 6, in some signal processing circuitry 602 is electrically coupled to image sensor 316 to receive electrical signals generated by image sensor 316. In some embodiments, signal processing circuitry 602 can include one or more charge storage elements, an analog signal readout circuitry, and a digital control circuitry. In some embodiments, the charge storage elements receive or read out electrical signals generated in parallel based on substantially all photosensitive elements of image sensor 316 (e.g., using a global shutter); and transmit the received electrical signals to the analog signal read-out circuitry. The analog signal read-out circuitry may include, for example, an analog-to-digital converter (ADC), which converts analog electrical signals to digital signals.

Using a global shutter in signal processing circuitry 602 can improve the signal readout speed over a rolling shutter. A rolling shutter exposes different rows of an image sensor array at different times and reads out in a chosen sequence. In a rolling shutter, although each row of the image sensor may be subject to the same exposure time, the rows at the top of the image sensor may end the exposure before the rows at the bottom of the image sensor. This may lead to spatial distortion, especially for large scale image sensing systems. A global shutter can expose all photosensitive elements (e.g., pixels) simultaneously or at substantially the same time. At the end of the exposure, the collected charge or electrical signal can be transferred to the readout nodes of the analog signal readout circuitry simultaneously or at substantially the same time. As a result, using a global shutter enables eliminating or reducing spatial distortion, especially for large scale sensing systems. In some embodiments, eliminating or reducing spatial distortion can have significantly positive impact on high-throughput DNA sequencing, which frequently relies on high-resolution detection of large amounts of fine targets at high density. Global shutter techniques can improve the accuracy of co-registration of a large quantity (e.g., millions) of DNA image spots on many (e.g., thousands) sequencing images repeatedly recorded at different testing times.

As shown in FIG. 6, after signal processing circuitry 602 converts analog electrical signals to digital signals, it can transmit the digital signals to a data processing system 604 for further processing. For example, data processing system 604 can perform various digital signal processing (DSP) algorithms (e.g., compression) for high-speed data processing. In some embodiments, at least part of data processing system 604 can be integrated with signal processing circuitry 602 on the same semiconductor die or chip. In some embodiments, at least part of data processing system 604 can be implemented separately from signal processing circuitry 602 (e.g., using a separate DSP chip or cloud computing resources). Thus, data can be processed and shared efficiently to improve the performance of the sample analytical system. It is appreciated that at least a portion of signal processing circuitry 602 and data processing system 604 can be implemented using, for example, CMOS-based application specific integrated circuits (ASIC), field programmable gate array (FPGA), discrete IC technologies, and/or any other desired circuit techniques.

Figure 7A:
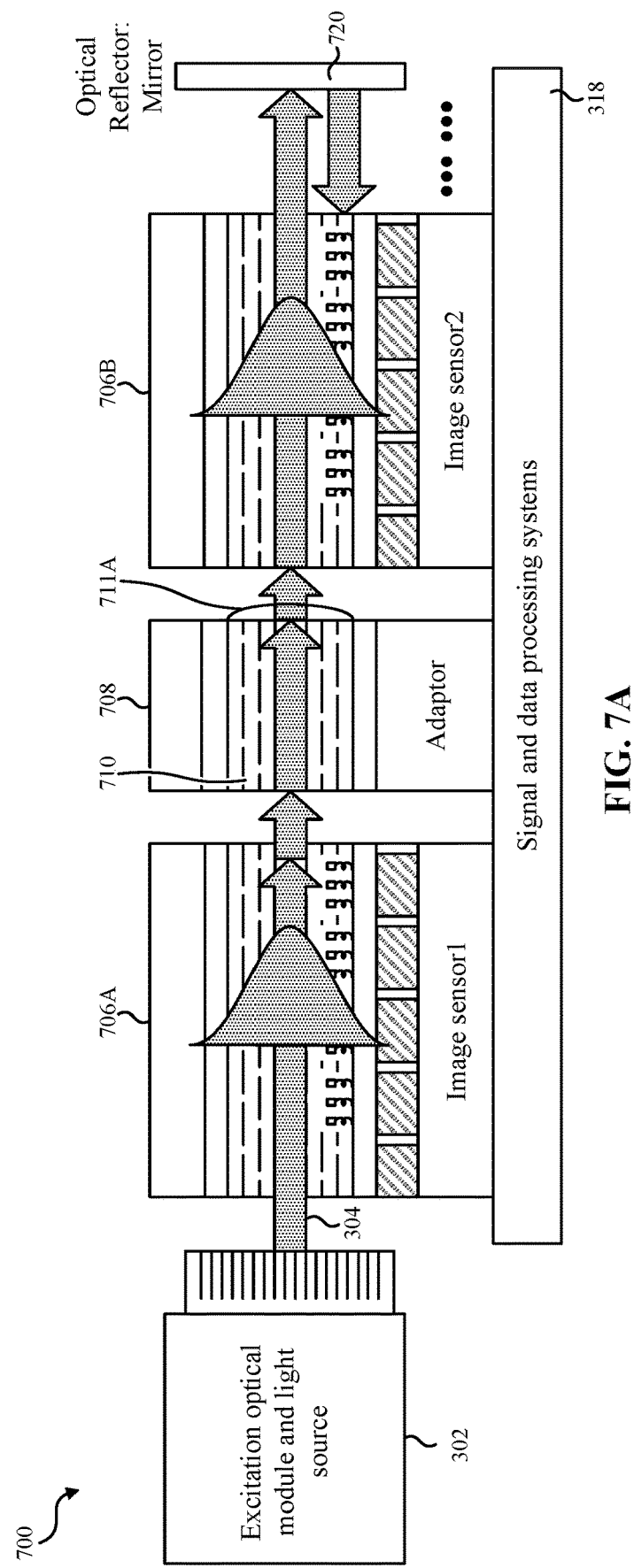
FIG. 7A illustrates an exemplary system configuration in which multiple liquid photonic systems and one or more coupling adaptors are mounted on a single printed circuit board (PCB).

FIG. 7A illustrates an exemplary analytical system 700 including a plurality of liquid photonic systems and one or more coupling adaptors. As illustrated in FIG. 7A, similar to those described above, analytical system 700 can also include an excitation optical module and light source 302, which provides an excitation light 304. In some embodiments, analytical system 700 includes a plurality of liquid photonic systems 706A-N (collectively as 706). For example, FIG. 7A illustrates two such liquid photonic systems 706A and 706B. Each of the plurality of liquid photonic systems 706 can include components or subsystems the same as or similar to those in any one of liquid photonic systems 300A-D as described above. For example, each of liquid photonic system 706A and 706B can include a fluid-resistant substrate, an optical waveguide containing a fluidic reaction channel, a filter (with or without a grid structure), and an image sensor. In some embodiments, each of liquid photonic system 706A and 706B can further include gasket for liquid sealing and inlet/outlet for reagent exchange. These components and sub-systems can be the same or similar to those described above, and are thus not repeatedly described.

Analytical system 700 can further include one or more adaptors 708 for coupling two adjacent liquid photonic systems. As illustrated in FIG. 7A, adaptor 708 can be disposed between liquid photonic system 706A and liquid photonic system 706B to couple the two systems 706A and 706B. For example, adaptor 708 can include an adaptor optical waveguide 711A optically coupled to an optical waveguide of the preceding liquid photonic system 706A and an optical waveguide of the following liquid photonic system 706B. The adaptor optical waveguide 711A is configured to deliver the excitation light 304 from the preceding liquid photonic system 706A to the following liquid photonic system 706B. Thus, the excitation light 304 (or a portion thereof) delivered to a preceding liquid photonic system can be effectively reused by a following liquid photonic system. In some embodiments, the adaptor optical waveguide device 711A can be, for example, an optical fiber connecter that has a low transmission loss. In some embodiments, these adaptors can be eliminated by using a single optical waveguide (e.g., a single large waveguide) covering multiple image sensors. Therefore, the light energy loss from preceding liquid photonic system 706A to the following liquid photonic system 706B can be significantly reduced or minimized. In some embodiments, following the last liquid photonic system, an optical reflector mirror 720 can be disposed to reflect the excitation light (or a portion thereof) back to the optical waveguides of the plurality liquid photonic systems (e.g., systems 706A and 706B). The optical reflector mirror 720 thus further improves the excitation light reuse efficiency. In some embodiments, the optical reflector mirror 720 can also improve the light uniformity across the image sensors of the liquid photonic systems and improves the intensity of the light received for at least some of image sensors.

As discussed above, in some embodiments, an optical waveguide (e.g., optical waveguide 311A-D) can include a fluidic reaction channel (e.g., either as an optical core layer or cladding layer of the optical waveguide). Similarly, adaptor optical waveguide 711A can include an adaptor fluidic channel 710. The adaptor fluidic channel 710 can be coupled to a fluidic reaction channel of the preceding liquid photonic system 706A and a fluidic reaction channel of the following liquid photonic system 706B. The adaptor fluidic channel 710 is configured to deliver reagents from the preceding liquid photonic system 706A to the following liquid photonic system 706B. As a result, reagents can be used sequentially on each liquid photonic system to save consumable cost. Moreover, high concentration reagents for base incorporation and cleavage buffer are often required for fast chemical reactions inside the fluidic reaction channel.

Under certain circumstances, only a very minor portion of chemicals included in the reagent may be consumed. Thus, reusing these high-concentration high-cost reagent can improve reaction time with reduced consumable cost. As discussed above, the separation of different reagents in sequentially coupled fluidic reaction channels can rely on a microfluidics system using air gaps between different reagents (e.g., buffer solutions). The microfluidic system can include pumps and valves for switching reagents and producing air gaps, as illustrated in FIG. 2.

In some embodiments, as illustrated in FIG. 7A, the image sensors of the plurality of liquid photonic systems 706 (e.g., 706A and 706B) can transmit electrical signals to the same signal and data processing systems 318. As a result, samples disposed in the plurality of liquid photonic systems 706 can be processed in parallel on a large_scale. This improves the testing throughput and speed over conventional analytical systems (e.g., a gene sequencing system). Further, as discussed above, liquid photonic systems 706 can use the optical waveguide techniques and the BSI-based image sensing techniques as discussed above, which enable the liquid photonic systems to be scaled or stacked up to provide parallel signal and data processing in a large-scale imaging application (e.g., 100 meg-1 giga imaging application). In some embodiments, the plurality of liquid photonic systems 706 can be electrically integrated on a single printed circuit board (PCB). For example, a single PCB may integrate about 1-20 liquid photonic systems 706, thereby scaling up the imaging area. Using 20 liquid photonic systems 706 as an example, 20 liquid photonic systems 706 integrated on a PCB can provide 20 times more imaging area due to the increased number of photosensitive elements (e.g., pixels) included in the 20 image sensors of the 20 liquid photonic systems 706. As an example, if each image sensor of a liquid photonic system 706 has 100 meg pixels, 20 liquid photonic systems 706 integrated on a PCB would have 2000 meg or 2 giga pixels, thereby greatly improving the testing throughput and speed. The testing throughput and speed, and in turn, testing efficiency, can further be improved by using (e.g., stacking) more PCBs containing more liquid photonic systems, as discussed below.

Figure 7B:
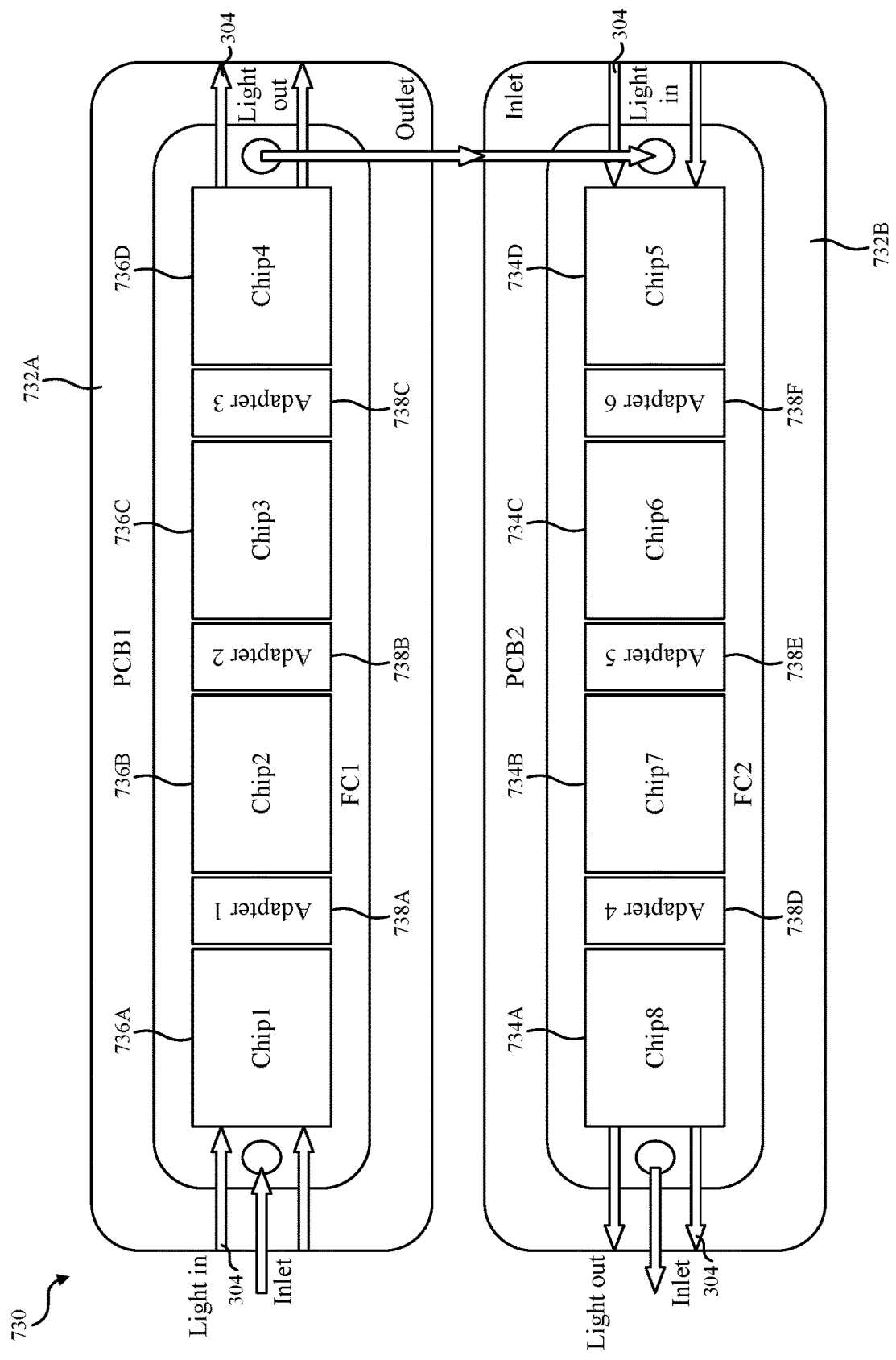
FIG. 7B illustrates an exemplary system configuration in which multiple liquid photonic systems and one or more coupling adaptors are mounted on multiple printed circuit boards (PCBs).

FIG. 7B illustrates an exemplary analytical system 730 in which multiple liquid photonic systems and one or more coupling adaptors are mounted on multiple printed circuit boards (PCBs). As illustrated in FIG. 7B, analytical system 730 may include, for example, two PCBs: PCB 732A and PCB 732B. Each of the PCBs 732A and 732B may integrate, for example, 4 liquid photonic systems (e.g., 736A-D and 734A-D respectively). Each of the liquid photonic systems 736A-D and 734A-D can be the same or similar to those described in FIG. 7A (e.g., systems 706A and 706B), and are thus not repeatedly described. As shown in FIG. 7B, adaptors 736A-F can be disposed to couple two adjacent liquid photonic systems, similar to those described above. In some embodiments, excitation light 304 can be delivered to the first liquid photonic system 736A of PCB 732A, and can travel through the liquid photonic systems 736B-D on PCB 732A. The excitation light 304 can then be directed toward PCB 732B using, for example, additional optical coupling devices such as grating(s), mirror(s), prism(s), fiber(s) diffuser(s), and other optical coupling devices. The excitation light 304 can then be received at liquid photonic system 734D on PCB 732A, and travel through the liquid photonic systems 734A-C to provide illumination of the samples disposed in these systems. In some embodiments, multiple optical waveguides associated with multiple liquid photonic systems can form a light or illumination path in the range of about several millimeters (e.g., about 5 mm) to several meters (e.g., about 5 m). As discussed above, the optical waveguides can be disposed above a BSI-based image sensor. In some embodiments, an optical waveguide (or at least a part thereof) is detachable from the BSI-based image sensor, thereby providing flexibility of replacing the optical waveguides (which can include a fluidic reaction channel) while preserving the BSI-based image sensor.

In a similar manner as shown in FIG. 7B, the reagent can be delivered through the liquid photonic systems from one PCB to another. As discussed above, the reagent is delivered through the liquid reaction channels of the multiple liquid photonic systems, in which chemical reaction can occur during an imaging period (e.g., light sensing or illumination period) and in which reagent exchange can occur between the imaging periods. As a result, the testing throughput and speed, and in turn, the testing efficiency, can be significantly improved using multiple PCBs with multiple liquid photonic systems integrated on each PCB. This configuration also improves the imaging area due to the increased number of photosensitive elements (e.g., pixels) included in the image sensors. For instance, in FIG. 7B, if each image sensor of a liquid photonic system 734 or 736 has 100M pixels, and if 5 PCBs are used in system 730, the overall analytical system 730 would have 2000 Meg or 2 Giga pixels, thereby further improving the testing throughput and speed. As discussed above, the data obtained from the image sensors can then be converted to digital signals and processed locally in the analytical system 730 or remotely (e.g., on cloud).

It is understood that the specific order or hierarchy of blocks in the processes and/or flowcharts disclosed is an illustration of exemplary approaches. Based upon design preferences, it is understood that the specific order or hierarchy of blocks in the block diagrams, processes and/or flowcharts may be rearranged. Further, some blocks may be combined or omitted. The accompanying method claims present elements of the various blocks in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module," "mechanism," "element," "device," and the like may not be a substitute for the word "means." As such, no claim element is to be construed under 35 U.S.C. § 112(f) unless the element is expressly recited using the phrase "means for."

What is claimed is:

1. A system for analyzing biological samples that are luminescent or luminescently-labeled biomolecules including at least one of nucleic acids, nucleotides, deoxyribonucleic acid (DNA), ribonucleic acid (RNA), peptide, or proteins, the system comprising:
    an optical waveguide extending along a length, and including:
        a first end, wherein the optical waveguide is configured to receive an excitation light having a plurality of wavelength ranges or a plurality of discrete wavelengths at the first end of the optical waveguide,
        a second end opposite to the first end,
        a first light-guiding layer disposed between the first end and the second end, wherein:
            the first light-guiding layer is an optical core layer of the optical waveguide, and
            the first light-guiding layer is configured to direct, at least in part, the received excitation light toward the second end of the optical waveguide along a longitudinal direction of the optical waveguide,
        a fluidic reaction channel bounded in part by the first light-guiding layer of the optical waveguide, wherein:
            the fluidic reaction channel containing a liquid reagent is a first optical cladding layer of the optical waveguide,
            the liquid reagent is held in the fluidic reaction channel,
            the fluidic reaction channel is configured to allow flow of the liquid reagent, and,
            the first light-guiding layer has a refractive index that is greater than a refractive index of the fluidic reaction channel containing the liquid reagent, such that the excitation light is substantially confined inside the first light-guiding layer,
        a second light-guiding layer bounded in part by the first light-guiding layer of the optical waveguide, wherein:
            the second light-guiding layer is configured to be a second optical cladding layer of the optical waveguide, and
            the second light-guiding layer has a refractive index that is less than the first light-guiding layer;
        wherein the optical waveguide is configured to deliver the excitation light to biological samples disposed in the fluidic reaction channel and on a surface of the first light-guiding layer;
    an image sensor optically coupled to the optical waveguide, wherein the image sensor is configured to detect at least a portion of light emitted from the biological samples as a result of the excitation light, the image sensor including:
        a plurality of photosensitive elements disposed at a first distance to the optical waveguide, and
        a plurality of conducting layers disposed at a second distance to the optical waveguide, wherein first distance is less than the second distance; and
        a filter disposed between the optical waveguide and the image sensor, the filter having a plurality of filter cells, wherein the plurality of filter cells includes a plurality of filter cells of a first type and a plurality of filter cells of a second type,
    wherein the plurality of filter cells of the first type are configured to remove a portion of the excitation light having a first wavelength range of the plurality of wavelength ranges or at least one discrete wavelength of the plurality of discrete wavelengths,
    wherein the plurality of filter cells of the second type are configured to substantially remove lights in all wavelength ranges reaching the plurality of filter cells of the second type, and
    wherein the plurality of filter cells of the first type and the plurality of filter cells of the second type are provided in a grid structure, being interleaved with one another to form a chessboard pattern configured to reduce crosstalk between adjacent photosensitive elements of the plurality of photosensitive elements.

2. The system of claim 1, further comprising a fluid-resistant substrate, wherein the fluid-resistant substrate includes at least one of a glass substrate or a plastic substrate.

3. The system of claim 1, further comprising a light source optically coupled to the first end of the optical waveguide, wherein the light source is configured to emit the excitation light.

4. The system of claim 1, further comprising a fluid-resistant substrate, wherein a first surface of the fluid-resistant substrate is in contact with the fluidic reaction channel of the optical waveguide.

5. The system of claim 4,
    wherein the first light-guiding layer is disposed at a third distance to the image sensor;
    wherein the second light-guiding layer is disposed at a fourth distance to the image sensor, wherein the third distance is greater than the fourth distance.

6. The system of claim 1, further comprising a fluid-resistant substrate,
    wherein the second light-guiding layer is disposed between the first light-guiding layer of the optical waveguide and the image sensor, and
    wherein the fluidic reaction channel is bounded at least in part by the first light-guiding layer and the fluid-resistant substrate.

7. The system of claim 1, wherein the first light-guiding layer includes a silicon nitride or tantalum pentoxide layer; and wherein the second light-guiding layer includes a polymer or silicon dioxide layer.

8. The system of claim 6,
    wherein the fluid-resistant substrate is disposed at a fifth distance to the image sensor;
    wherein the first light-guiding layer is disposed at a sixth distance to the image sensor, wherein the fifth distance is greater than the sixth distance.

9. The system of claim 1,
    further comprising a fluid-resistant substrate;
    wherein the second light-guiding layer is disposed between the fluid-resistant substrate and the first light-guiding layer of the optical waveguide; and wherein the fluidic reaction channel is further bounded at least in part by a second fluid-resistant substrate disposed between the fluidic reaction channel and the image sensor.

10. The system of claim 9,
wherein the first light-guiding layer is disposed at a seventh distance to the image sensor; and
wherein the second fluid-resistant substrate is disposed at an eighth distance to the image sensor, wherein the seventh distance is greater than the eighth distance.

11. The system of claim 1,
wherein the first light-guiding layer comprises a fluid-resistant substrate; and
wherein the fluidic reaction channel is bounded at least in part by the first light-guiding layer and by a second fluid-resistant substrate disposed between the fluidic reaction channel and the image sensor.

12. The system of claim 11, further comprising a chamber housing at least a part of the optical waveguide;
wherein the fluid-resistant substrate of the first light-guiding layer is configured to be the optical core layer of the optical waveguide;
wherein a gas filled within the chamber forms at least a part of the second optical cladding layer; and
wherein the gas filled within the chamber and the first optical cladding layer substantially confine the excitation light inside the optical core layer.

13. The system of claim 11,
wherein the first light-guiding layer is disposed at a ninth distance to the image sensor; and
wherein the second fluid-resistant substrate is disposed at a tenth distance to the image sensor, wherein the ninth distance is greater than the tenth distance.

14. The system of claim 1, further comprising an actuator mechanically coupled to the optical waveguide, wherein the actuator is electrically, pneumatically, or hydraulically powered to adjust a thickness of the fluidic reaction channel in accordance with different operating modes of the system.

15. The system of claim 1:
wherein the photosensitive elements of the image sensor are configured to:
detect photons of the at least a portion of light emitted from the biological samples as a result of the excitation light,
generate electrical signals based on the detected photons; and
wherein the conducting layers conduct the generated electrical signals.

16. The system of claim 1, further comprising:
a signal processing circuitry electrically coupled to the image sensor, the signal processing circuitry includes one or more charge storage elements, an analog signal read-out circuitry, and a digital control circuitry.

17. The system of claim 16, wherein the charge storage element of the signal processing circuitry is configured to:
receive electrical signals generated in parallel based on substantially all photosensitive elements of the image sensor; and
transmit the received electrical signals to the analog signal read-out circuitry, wherein the electrical signals are converted to digital signals.

18. The system of claim 16, wherein the image sensor is disposed in a first semiconductor die, wherein the signal processing circuitry is disposed in a second semiconductor die, and wherein the first semiconductor die is stacked on top of the second semiconductor die.

19. The system of claim 1, wherein the luminescent or luminescently-labeled biomolecules include luminescent markers capable of emitting light in one, two, or three wavelength ranges.

* * * * *